United States Patent
Barsoum

(10) Patent No.: US 8,148,426 B2
(45) Date of Patent: Apr. 3, 2012

(54) BIS(THIO-HYDRAZIDE AMIDES) FOR INCREASING HSP70 EXPRESSION

(75) Inventor: James Barsoum, Lexington, MA (US)

(73) Assignee: Synta Pharmaceuticals Corp., Lexington, MA (US)

(*) Notice: Subject to any disclaimer, the term of this patent is extended or adjusted under 35 U.S.C. 154(b) by 605 days.

(21) Appl. No.: 11/281,923

(22) Filed: Nov. 17, 2005

(65) Prior Publication Data

US 2006/0142386 A1 Jun. 29, 2006

Related U.S. Application Data

(60) Provisional application No. 60/629,595, filed on Nov. 19, 2004.

(51) Int. Cl.
*A61K 31/16* (2006.01)
(52) U.S. Cl. .................................. 514/599; 514/614
(58) Field of Classification Search .............. 514/599, 514/614
See application file for complete search history.

(56) References Cited

U.S. PATENT DOCUMENTS

| | | |
|---|---|---|
| 4,012,360 A | 3/1977 | Schwarzenbach et al. |
| 6,013,836 A | 1/2000 | Hsu et al. |
| 6,172,108 B1 | 1/2001 | Vega et al. |
| 6,172,188 B1 | 1/2001 | Thastrup et al. |
| 6,235,787 B1 | 5/2001 | Broadhurst et al. |
| 6,365,745 B1 | 4/2002 | Matsui et al. |
| 6,399,659 B2 | 6/2002 | Usui et al. |
| 6,435,787 B1 | 8/2002 | John |

(Continued)

FOREIGN PATENT DOCUMENTS

DE 2037257 2/1972

(Continued)

OTHER PUBLICATIONS

Balkwill F and Mantovani A, "Inflammation and cancer: back to Virchow?" The Lancet, Feb. 2001, 357, 539-545.*

(Continued)

*Primary Examiner* — Brandon Fetterolf
*Assistant Examiner* — Paul Zarek
(74) *Attorney, Agent, or Firm* — McCarter & English, LLP; Steven G. Davis

(57) ABSTRACT

A method of treating a Hsp70-responsive disorder in a subject includes administering to the subject an effective amount of a compound represented by Structural Formula I, or a pharmaceutically acceptable salt or solvate thereof.

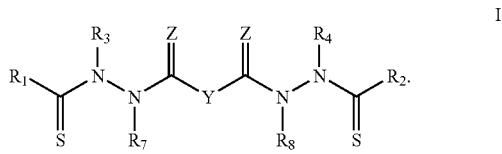

Y is a covalent bond or an optionally substituted straight chained hydrocarbyl group, or, Y, taken together with both >C=Z groups to which it is bonded, is an optionally substituted aromatic group.
$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.
$R_7$-$R_8$ are independently —H, an optionally substituted aliphatic group, or an optionally substituted aryl group.
Z is O or S.

22 Claims, 9 Drawing Sheets

U.S. PATENT DOCUMENTS

| | | | |
|---|---|---|---|
| 6,455,515 | B2 | 9/2002 | Gypser et al. |
| 6,656,971 | B2 | 12/2003 | Wu et al. |
| 6,703,426 | B1 | 3/2004 | Miles et al. |
| 6,762,204 | B2 | 7/2004 | Koya et al. |
| 6,800,660 | B2 | 10/2004 | Koya et al. |
| 6,825,235 | B2 | 11/2004 | Chen et al. |
| 6,924,312 | B2 | 8/2005 | Koya et al. |
| 7,001,923 | B2 | 2/2006 | Koya et al. |
| 7,037,940 | B2 | 5/2006 | Koya et al. |
| 7,074,952 | B2 | 7/2006 | Chen et al. |
| 2003/0045518 | A1 | 3/2003 | Koya et al. |
| 2003/0119914 | A1* | 6/2003 | Koya et al. ............ 514/614 |
| 2003/0195258 | A1 | 10/2003 | Koya et al. |
| 2004/0022869 | A1* | 2/2004 | Chen et al. ............ 424/623 |
| 2004/0225016 | A1 | 11/2004 | Koya et al. |
| 2005/0009920 | A1 | 1/2005 | Koya et al. |
| 2006/0116374 | A1 | 6/2006 | Koya et al. |
| 2006/0122183 | A1 | 6/2006 | Koya et al. |
| 2006/0135595 | A1 | 6/2006 | Koya et al. |
| 2006/0142393 | A1 | 6/2006 | Sherman et al. |
| 2006/0167106 | A1 | 7/2006 | Zhang et al. |
| 2006/0270873 | A1 | 11/2006 | Chen et al. |
| 2006/0281811 | A1 | 12/2006 | Chen et al. |
| 2007/0088057 | A1 | 4/2007 | Lunsmann et al. |

FOREIGN PATENT DOCUMENTS

| | | |
|---|---|---|
| FR | 2097737 | 4/1972 |
| GB | 1272920 | 5/1972 |
| JP | 50-91056 | 7/1975 |
| WO | WO 94/10995 | 5/1994 |
| WO | WO 99/34796 | 7/1999 |
| WO | WO 03/006428 A | 1/2003 |
| WO | WO 03/006430 * | 1/2003 |
| WO | WO 03/006430 A | 1/2003 |
| WO | WO 03/047524 * | 12/2003 |
| WO | WO 2004/064826 A1 | 8/2004 |
| WO | WO 2006/009940 A1 | 1/2006 |
| WO | WO 2006/033913 A2 | 3/2006 |
| WO | WO 2006/113493 A2 | 10/2006 |
| WO | WO 2006/113572 A1 | 10/2006 |
| WO | WO 2006/113695 A1 | 10/2006 |

OTHER PUBLICATIONS

Jacquier-Sarlin MR, Fuller K, Dinh-Xuan AT, Richard MJ, and Polla BS, "Protective effects of hsp70 in inflammation," Experientia, Nov. 1994, 50(11-12), 1031-1038.*

Calderwood SK, Mambula SS, and Gray PJ Jr, "Extracellular heat shock proteins in cell signaling and immunity," Annals of the New York Academy of Sciences, Oct. 2007, 1113, 28-39.*

Daniels GA, Sanchez-Perez L, Diaz RM, Kottke T, Thompson J, Lai M, Gough M, Karim M, Bushell A, Chong H, Melcher A, Harrington K, Vile RG, "A simple method to cure established tumors by inflammatory killing of normal cells," Nature Biotechnology, Sep. 2004, 22(9), 1125-1132 (Epub Aug. 1, 2004).*

Tanaka S, Kimura Y, Mitani A, Yamamoto G, Nishimura H, Spallek R, Singh M, Noguchi T, and Yoshikai Y, "Activation of T cells recognizing an epitope of heat-shock protein 70 can protect against rat adjuvant arthritis," Journal of Immunology, Nov. 1999, 163(10), 5560-5565.*

Kimura Y, Yamada K, Sakai T, Mishima K, Nishimura H, Matsumoto Y, Singh M, and Yoshikai Y, "The regulatory role of heat shock protein 70-reactive CD4+ T cells during rat listeriosis," International Immunology, Feb. 1998, 10(2), 117-130.*

Ashburner, M. and Bonner, J.J., "The Induction of Gene Activity in Drosophila by Heat Shock," Cell, 17: 241-254 (1979).

Auluck, P.K., et al., "Chaperone Suppression of α-Synuclein Toxicity in a Drosophila Model for Parkinson's Disease," Science, 295: 865-868 (2002).

Barclay, J.W. and Roberson,R.M., "Role for Calcium in Heat Shock-Mediated Synaptic Thermoprotection in Drosophila Larvae," J. Neurobiol., 56(4): 360-371 (2003).

Barry, V.C., et al., "Anticancer Agents—III. Synthesis and Anticancer Activity of Some Bis-Thiosemicarbazones and Thoiosemicarbazides," Proc. R.I.A. 65:309-324 (1967).

Beck, F-X., et al., "Molecular Chaperones in the Kidney: Distribution, Putative Roles, and Regulation," Am. J. Physiol. Renal. Physiol., 279: F203-F215 (2000).

Bellmann, K., et al., "Heat Shock Induces Resistance in Rat Pancreatic Islet Cells against Nitric Oxide, Oxygen Radicals and Streptozotocin Toxicity in Vitro," J. Clin. Invest., 95(6): 2840-2845 (1995).

Blondeau, N., et al., "Polyunsaturated Fatty Acids Induce Ischemic and Epileptic Tolerance," Neuroscience, 109(2): 231-241 (2002).

Carmel, J.B., et al., "Mediators of Ischemic Preconditioning Identified by Microarray Analysis of Rat Spinal Cord," Exp. Neurol., 185: 81-96 (2004).

Carter, R. J., et al., "Characterization of Progressive Motor Deficits in Mice Transgenic for the Human Huntington's Disease Mutation," J. Neuroscience, 19(8): 3248-3257 (1999).

Chen, H-C., et al., Induction of Heat Shock Protein 70 Protects Mesangial Cells Against Oxidative Injury, Kidney Int., 56: 1270-1273 (1999).

Chuyguk, V. A. and Nemazanyj A.G., "Mesoionic Methine Dyes from Biquaternary Salts of Dihetarylmethanes—1,3,4-Oxa(thia)diazoles and 1,2,4-Triazoles Derivatives," Ukr. Khim. Zhurn. 48:520 (1984). Translation submitted in U.S. Appl. No. 10/193,075, filed Jul. 10, 2002.

Craig, E. A., "The Heat Shock," Crit. Rev. Biochem., 18(3): 239-280 (1985).

Doi, Y., et al., "Effect of HSP70 Induced by Warm Ischemia to the Liver on Liver Function after Partial Hepatectomy," Hepato-Gastroenterology, 48: 533-540 (2001).

Gao, Y., et al., "Protein Kinase C-dependent Activation of P44/42 Mitogen-activated Protein Kinase and Heat Shock Protein 70 in Signal Transduction During Hepatocyte Ischemic Preconditioning," World J. Gastroenterol., 10(7): 1019-1027 (2004).

Georgopoulos, C. and Welch, W. J., "Role of the Major Heat Shock Proteins as Molecular Chaperones," Annu. Rev. Cell Biol., 9: 601-634 (1993).

Goodman & Gilman's, The Pharmacological Basis of Therapeutics, Ninth Edition, (1996), Section X, Calabresi et al., pp. 1225-1232 (1996).

Gurney, M. E., et al., "Motor Neuron Degeneration in Mice That Express a Human Cu,Zn Superoxide Dismutase Mutation," Science, 264: 1772-1775 (1994).

Hiratsuka, M., et al., "Heat Shock Pretreatment Protects Pulmonary Isografts from Subsequent Ischemia-reperfusion Injury," J. Heart Lung Transplant, 17 (12): 1238-1246 (1998).

Holcomb, L., et al., "Accelerated Alzheimer-Type phenotype in transgenic mice carrying both mutant amyloid precursor protein and presenilin 1 transgenes," Nature Medicine, 4(1): 97-100 (1998).

Howland, D. S., et al., "Focal Loss of the Glutamate Transporter Eaat2 in a Transgenetic Rat Model of Sod1 Mutant-mediated Amyotrophic Lateral Sclerosis (ALS)," Proc. Nat. Acad. Sci. USA, 99(3): 1604-1609 (2002).

Ishii, Y., et al., "Retinal Ganglion Cell Protection with Geranylgeranylacetone, a Heat Shock Protein Inducer, in a Rat Glaucoma Model," Invest. Opthalmol. Vis. Sci., 44(5): 1982-1992 (2003).

Johnson, A.D., et al., "Differential Distribution of 70-kD Heat Shock Protein Atherosclerosis," Arterio Thromb Vasc Biol, 15(1): 27-36 (1995).

Kandror, O. and Goldberg, A.L., "Trigger Factor is Induced Upon Cold Shock and Enhances Viability of Escherichia coli at Low Temperatures," Proc Natl Acad Sci USA, 94(10): 4978-4981 ( 1997).

Kelly, S. and Yenari, M.A., "Neuroprotection: Heat Shock Proteins," Curr Res Med Opin, 18(Suppl. 2): s55-s60 (2002).

Keswani, et al., "FK506 Is Neuroprotective in a Model of Antiretroviral Toxic Neuropathy," Annals Neurology, 53(1): 57-64 (2003).

Kiang, J.G. and Tsokos, G.C., "Heat Shock Protein 70 kDA: Molecular Biology, Biochemistry, and Physiology," Pharmacol Ther, 80(2): 183-201 (1998).

Klettner, A., "The Induction of Heat Shock Proteins as a Potential Strategy to Treat Neurodegenerative Disorders," Drug News Perspect, 17(5): 299-306 (2004).

Klettner, A. and Herdegen, T., "The Immunophilin-Ligands FK506 and V-10,367 Mediate Neuroprotection by the Heat Shock Response," *Br J Pharmacol*, 138(5): 1004-1012 (2003).

Langston, J.W., et al., "Selective Nigral Toxicity After Systemic Administration of 1-Methyl-4Phenyl-1,2,5,6-Tetrahydropyrine (MPTP) in the Squirrel Monkey," *Brain Res*, 292: 390-394 (1984).

Lee, J.E., et al., "Differential Neuroprotection From Human Heat Shcok Protein 70 Overexpression in in Vitro and in Vivo Models of Ischemia and Ischemia-Like Conditions, "*Exp Neurol*, 170(1): 129-139 (2001).

Lepore, D.A., et al., "Role of Priming Stresses and Hsp70 in Protection From Ischemia-Reperfusion Injury in Cardiac and Skeletal Muscle," *Cell Stress & Chaperones*, 6(2): 93-96 (2001).

Lindquist, S., "The Heat-Shock Response," *Ann Rev Biochem*, 55: 1151-1191 (1986).

Longa, E.Z., et al., "Reversible Middle Cerebral Artery Occlusion Without Craniectomy in Rats," *Stroke*, 20(1): 84-91 (1989).

Malberg, J.E. and Seiden, L.S., Poster "MDMA Administration Induces Expression of HSP70 in the Rat Brain." Society for Neuroscience Annual Meeting, New Orleans, LA, Oct. 25-30, 1997.

Mangiarini, L., et al. , "Exon 1 of the *HD* Gene With an Expanded CAG Repeat is Sufficient to Cause a Progressive Neurological Phenotype in Transgenic Mice," *Cell*, 87: 493-506 (1996).

Marber, M.S., et al., "Overexpression of the Rat Iducible 70-kD Heat Stree Protein in a Transgenic Mouse Increases the Resistance of the Heart to Ischemic Injury," *J Clin Invest*, 95: 1446-1456 (1995).

Minowada, G. and Welch, W.J., "Clinical Implications of the Stress Response," *J Clin Invest*, 95: 3-12 (1995).

Molina, P., et al., "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s* 5:1159-1166 (1991).

Molina, P., et al., "Preparation of a Novel Type of Ligands Incorporating Two or Three 1,3,4-Thiadiazole Units," *Heterocycles* 36(6):1263-1278 (1993).

Morimoto, et al., In: The Biology of Heat Shock Proteins and Molecular Chaperone. (NY: Cold Spring Harbor Laboratory Press) pp. 417-455 (1994).

Mosser, D.D., et al., "The Chaperone Function of hsp70 Is Required for Protecti Induced Apoptosis," *Mol Cell Biol*, 20(19): 7146-7159 (2000).

O'Callaghan, C. N., "Anticancer Agents—X. Cyclisation of 1-Acyl-4-Alkylthiosemicarbazide Derivatives to 1,2,4-Triazoline-3-Thiones in the Presence of Hydrazine," *Proc. R.I.A.* 74:455-461 (1974).

Plumier, J.-C. L., et al., "Transgenic Mice Expressing the Human Heat Shock Protein 70 Have I proved Post-Ischemic Myocardial Recovery," *J Clin Invest*, 95: 1854-1860 (1995).

Radford, N.B., et al., "Cardioprotective Effects of 70-kDa Heat Shock Proteiin in Transgenic Mice," *Proc Natl Acad Sci USA*, 93(6): 2339-2342 (1996).

"Remarks" paper as submitted by applicant's attorney.

Renshaw, G.M.C., et al., "Oxygen Sensors and Energy Sensors Act Synergistically to Achieve a Graded Alteration in Gene Expression: Consequences for Assessing the Level of Neuroprotection in Response to Stressors," *Front Biosci*, 9: 110-116 (2004).

Sato, K., et al., "HSP70 is Essential to the Neuroprotective Effect of Heat-Shock," *Brain Res*, 740(1-2): 117-123 (1996).

Sauer, H. and Oertel, W.H., "Progressive Degeneration of Nigrostriatal Dopamine Neurons Following Instrastriatal Terminal Lesions with 6-Hydroxydopamine: A Combined Retrograde Tracing and Immunocytochemical Study in the Rat," *Neuroscience*, 59(2): 401-415 (1994).

Simon, M.M., et al., "Heat Shock Protein 70 Overexpression Affects the Response to Ultraviolet Light in Murine Fibroblasts," *J Clin Res*, 95(3): 926-933 (1995).

Sobue, G., Molecular Pathogenesis of Motor Neuron Diseases (in Japanese) English abstract, *Nihon Shinkei Seishin Yakurigaku Zasshi*, 21(1): 21-25 (2001).

Stalteri, M.A., et al., "Site-specific conjugation and labelling of prostate antibody 7E11C5.3 (CYT-351) with technetium-99m," *Eur J. Nucl Med* 24(6):651-654 (1997).

Tavaria, M. et al., "A Hitchhiker's Guide to the Human Hsp70 Family," *Cell Stress Chaperones*, 1(1): 23-28 (1996).

Todryk, S.M., et al. "Facets of Heat Shock Protein 70 Show Immunotherapeutic Potential,", *Immunology*, 110(1): 1-9 (2003).

Twomey, D., "Anticancer Agents-IX. Derivatives of Pyridine, Pyridazine and Phthalazine," *Proceedings of the Royal Irish Academy*, vol. 74, Sect. B:37-52,(1974).

Tsuchiya, D., et al., "Overexpression of Rat Heat Shock Protein 70 Reduces Neuronal injury After Transient Focal Ischemia, Transient Global Ischemia, or Kainic Acid-Induced Seizures," *Neurosurgery*, 53(5): 1179-1187 (2003).

Vleminckx, V., et al., "Upregulation of HSP27 in a Transgenic Model of ALS," *J Neuropathol Exp Neurol*, 61(11): 968-974 (2002).

Voss, R.M., et al., "Gender Differences in the Expression of Heat Shock Proteins: The Effect of Estrogen," *Am J Physiol Heart Circ Physiol*, 285: H687-H692 (2003).

Yenari, M.A., "Heat Shock Proteins and Neuroprotection," *Adv Exp Med Biol*, 513: 281-299 (2002).

Yu, Q., et al., "Retinal Uptake of Intravitreally Injected Hsc/Hsp70 and its Effect on Susceptibility to Light Damage," *Molecular Vision*, 7: 48-56 (2001).

Zhang, Y., et al., "Estrogen and Androgen Protection of Human Neurons Against Intracellular Amyloid $\beta_{1-42}$ Toxicity Through Heat Shock Protein 70," *J Neuroscience*, 24(23): 5315-5321 (2004).

Al-Talib, M. et al., "Diacyl Acid Dihydrazides," Magnetic Resonance in Chemistry 28:1072-1078 (1990).

Asahi Chemical Ind. KK. Abstract of Japanese Patent No. 50-91056, Accession No. 47521Y/27 (1975).

Barrett, William G. and McKay, Donald, "Decomposition and Cycloaddition Reactions of Some Bis(azodicarbonyl) Compounds," Journal of Chem. Soc. (4):1046-1052 (1975).

Chuiguk, V.A., and Nemazanyi, A.G., "Mesoionic Methine Dyes of Biquaternary Salts of Diheteroaryl Methanes—Derivatives of 1, 3, 4—oxa (thia) Diazoles and 1, 2, 4—Triazoles," Kiev. Gos. Univ., Kiev, USSR, Ukrainskii Khimicheskii Zhurnal, Russian Edition, 50(5):519-524 (1984). Abstract, Accession No. 1984:630420, HCAPLUS Database.

H. Bräuniger, "Hydrazide and Hydrazidderivate von Dicarbonsäuren," Pharmaceutical-Chemical Institute of University of Rostock, Supplied by the "British Library" 25(5-6) 279-283 (1970).

Honshu Paper Mfg. Co. Ltd, Abstract of Japanese Patent No. 182050, published Feb. 13, 1996.

Merlin, J.L., et al., In Vitro Comparative Evaluation of Trastuzumab (Herceptin®) Combined with Paclitaxel (Taxol®) or Docetaxel (Taxotere®) in HER2-Expressing Human Breast Cancer Cell Lines, *Annals of Oncology* 13: 1743-1748 (2002).

Mitsui Toatsu Chem. Inc., Abstract of Japanese Patent No. 308024, published Dec. 25, 1986. from Derwent Publications Ltd.

Rupp, Walter, CA76:126992, 1972.

Schwarz et al., CA77:48081, 1972.

\* cited by examiner

BIS(THIO-HYDRAZIDE AMIDES) FOR INCREASING HSP70 EXPRESSION

RELATED APPLICATION(S)

This application claims the benefit of U.S. Provisional Application No. 60/629,595, filed on Nov. 19, 2004. The entire teachings of the above application are incorporated herein by reference.

BACKGROUND OF THE INVENTION

Heat shock proteins (HSPs) are found in virtually all prokaryotic and eukaryotic cells. Increased expression of proteins in the Hsp 70 family are known to protect a broad range of cells under stress by inhibiting various cellular death pathways such as apoptosis (Mosser, et al., Mol Cell Biol. 2000 October; 20(19): 7146-7159; Yenari, Adv Exp Med Biol, 2002, 513, 281-299; Kiang and Tsokos, Pharmacol Ther. 1998; 80(2):182-201). Cells can experience stress due to temperature; injury (trauma); genetic disease; metabolic defects; apoptosis; infection; toxins; radiation; oxidants; excess/lack of nutrients or metabolic products; and the like. For example, it is known in the art that cells damaged in the following variety of medical conditions can experience a protective effect in response to Hsp70.

Protein misfolding/aggregation conditions resulting in neurodegeneration include Alzheimers' disease (Zhang, et al., J. Neuroscience, 2004, 24(23), 5315-5321; Klettner, Drug News Perspect, 2004 17(5), 299-306); Huntington's disease (Klettner, ibid); Parkinson's disease (Auluck, et al., Science, 2002, 295(5556), 865-868); and the like. Other neurodegenerative conditions include spinal/bulbar muscular atrophy (Sobue, Nihon Shinkei Seishin Yakurigaku Zasshi, 2001, 21(1), 21-25); and familial amyotrophic lateral sclerosis (Howland, et al., Proc Nat Acad Sci USA, 2002, 99(3), 1604-1609; Sobue, ibid; Vleminck, et al., J Neuropathol Exp Neurol, 2002, 61(11), 968-974).

Ischemia and associated oxidative damage affects diverse tissues including: neurons and glia (Carmel, et al., Exp Neurol, 2004, 185(1) 81-96; Renshaw and Warburton, Front Biosci, 2004, 9, 110-116; Yenari, Adv Exp Med Biol, 2002, 513, 281-299; Kelly and Yenari, Curr Res Med Opin, 2002, 18 Suppl 2, s55-60; Lee, et al., Exp Neurol, 2001, 170(1), 129-139; Klettner, ibid; Klettner and Herdegen, Br J Pharmacol, 2003, 138(5), 1004-1012); cardiac muscle (Marber, M. S., et al. (1995) J. Clin. Invest. 95:1446-1456; Plumier, J. C., et al. (1995) J. Clin. Invest. 95:1854-1860; Radford, N. B., et al. (1996) Proc. Natl. Acad. Sci. USA 93(6): 2339-2342; Voss, et al., Am J Physiol Heart Circ Physiol 285: H687-H692, 2003); liver tissue (Doi, et al., Hepatogastroenterology. 2001 March-April; 48(38):533-40; Gao, et al. World J Gastroenterol 2004; 10(7):1019-1027); skeletal muscle (Lepore et al., Cell Stress & Chaperones, 2001, 6(2), 93-96); kidney tissue (Chen, et al., Kidney Int. 1999; 56: 1270-1273; Beck, et al., Am J Physiol Renal Physiol 279: F203-F215, 2000.); pulmonary tissue (Hiratsuka, et al., J Heart Lung Transplant. 1998 December; 17(12):1238-46); pancreatic tissue (Bellmann, et al., J Clin Invest. 1995 June; 95(6): 2840-2845), and the like.

Siezure conditions that damage neurons include, e.g., epileptic siezure (Yenari, ibid; Blondeau, et al. Neuroscience 2002, 109(2), 231-241); or chemically induced siezure (Tsuchiya, et al., Neurosurgery, 2003, 53(5), 1179-1187).

Thermal stresses include hyperthermia conditions such as fever, heat stroke, and the like (Barclay and Robertson, J Neurobiol, 2003 56(4), 360-271; Sato, et al., Brain Res, 1996, 740(1-2), 117-123); and hypothermia (Kandor and Goldberg, Proc Natl Acad Sci USA. 1997 May 13; 94(10): 4978-4981).

Aging includes conditions such as atherosclerosis which affects smooth muscle cells (Minowada, G. and Welch, W. J. (1995) J. Clin. Invest. 95:3-12; Johnson, A. J., et al. (1995) Arterio. Thromb. Vasc. Biol. 15(1):27-36).

Other conditions include radiation damage, e.g., from ultraviolet light to tissues such as murine fibroblasts (Simon, M. M., et al. (1995) J. Clin. Res. 95(3): 926-933), and light damage to retinal cells (Yu, et, al, Molecular Vision 2001; 7:48-56).

Trauma includes, for example, mechanical injury, e.g., pressure damage to retinal ganglions in glaucoma (Ishii, et al., Invest Opthalmol Vis Sci, 2003, 44(5), 1982-1992).

Toxic conditions include doses of chemicals or biochemicals, for example, methamphetamine (Malberg & Seiden, Poster "MDMA Administration Induces Expression of HSP70 in the Rat Brain" Society for Neuroscience Annual Meeting, New Orleans, La., Oct. 25-30, 1997); antiretroviral HIV therapeutics (Keswani, et al., Annals Neurology, 2002, 53(1), 57-64); heavy metals, amino acid analogs, chemical oxidants, ethanol, glutamate, and other toxins (Ashburner, M. and Bonner, J. J. (1979) Cell: 17:241-254; Lindquist, S. (1986) Ann. Rev. Biochem. 55:1151-1191; Craig, E. A. (1985) Crit. Rev. Biochem. 18(3):239-280; Morimoto, et al., In: The Biology of Heat Shock Proteins and Molecular Chaperone, (1994) pp. 417-455. Cold Spring Harbor Laboratory Press. Cold Spring Harbor, N.Y.); and the like.

Therefore, there is a need for new methods of increasing expression of Hsp70 in order to treat disorders responsive to Hsp70.

SUMMARY OF THE INVENTION

Disclosed are methods employing bis(thio-hydrazide amides) to increase Hsp70 expression to treat Hsp70-responsive disorders. The bis(thio-hydrazide amides) can induce expression of Hsp70 in mice (see Example 3). Further, these compounds have favorable pharmacokinetic profiles and are transported throughout the body (see Examples 1 and 2), including crossing the blood-brain barrier.

A method of treating a Hsp70-responsive disorder in a subject includes administering to the subject an effective amount of a compound represented by Structural Formula I:

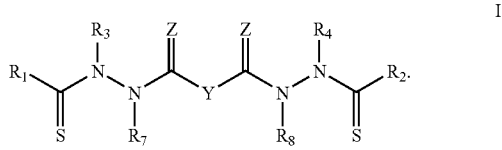

Y is a covalent bond or an optionally substituted straight chained hydrocarbyl group, or, Y, taken together with both >C=Z groups to which it is bonded, is an optionally substituted aromatic group.

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.

$R_7$-$R_8$ are independently —H, an optionally substituted aliphatic group, or an optionally substituted aryl group.

Z is O or S.

As used herein, the term "bis(thio-hydrazide amide)" also includes pharmaceutically acceptable salts and solvates of the compounds represented by Structural Formula I.

One embodiment of the invention is a method of treating a neurodegenerative disorder in a subject in need thereof, comprising administering to the subject an effective amount of the bis(thio-hydrazide amide).

Another embodiment of the invention is a method of reducing or preventing nerve damage in a subject at risk of nerve damage, comprising administering to the subject an effective amount of a compound of formula (I).

The methods described herein are believed to be effective for increasing expression of Hsp70 in order to treat Hsp70-responsive disorders.

DETAILED DESCRIPTION OF THE INVENTION

Figure 1:
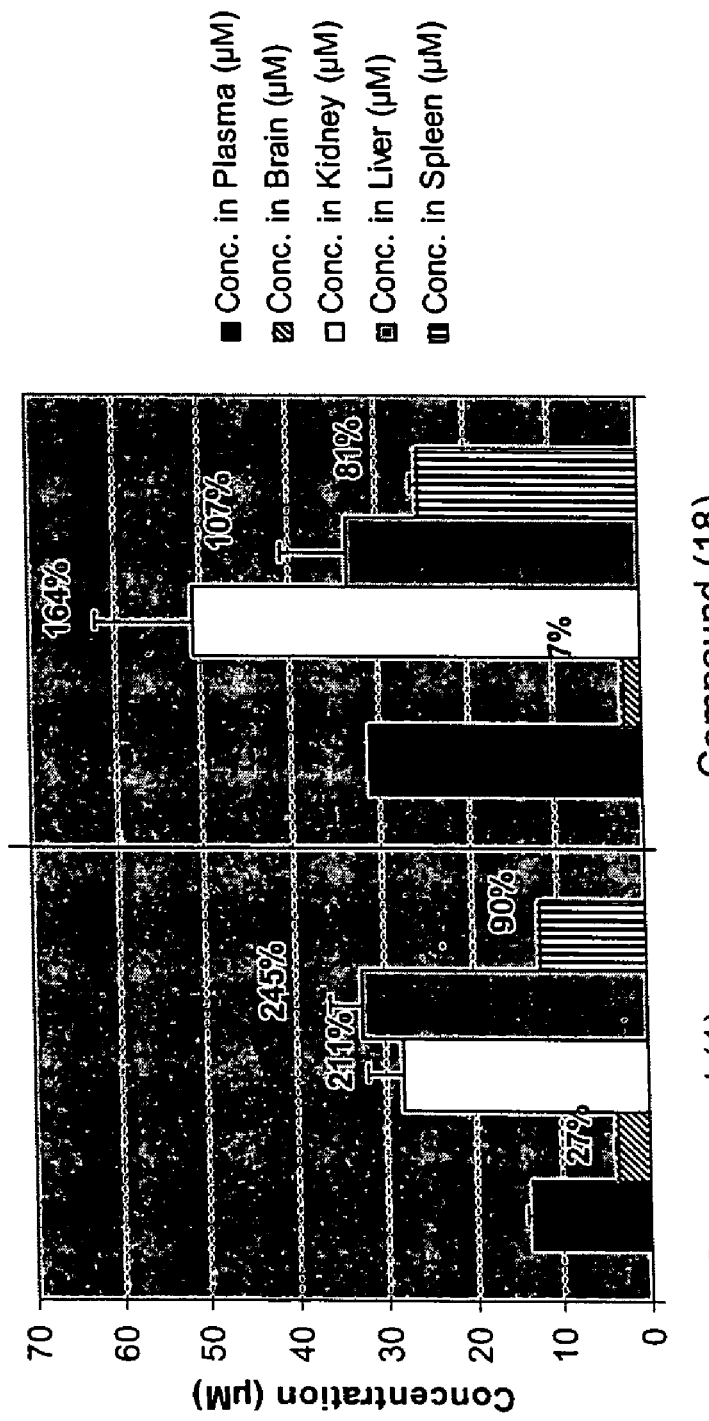
FIG. 1 is a bar graph showing the concentrations of compound (1) and compound (18) in mouse plasma, brain, kidney, liver and spleen measured 30 min after injection.

The bis(thio-hydrazide amides) employed in the disclosed invention are represented by Structural Formula I.

A "straight chained hydrocarbyl group" is an alkylene group, i.e., —(CH$_2$)$_y$—, with one, or more (preferably one) internal methylene groups is optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N(R$^a$)—), wherein R$^a$ is defined below. A preferred linkage group is —C(R$_5$R$_6$)—, wherein R$_5$ and R$_6$ are defined below. Suitable substitutents for an alkylene group and a hydrocarbyl group are those which do not substantially interfere with the biological activity of the disclosed compounds, examples of suitable substituents are as defined below. R$_5$ and R$_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C20 straight chained or branched alkyl group or a C3-C8 cyclic alkyl group is also referred to as a "lower alkyl" group. Examples of suitable substituents on aliphatic groups are as defined below.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." The term "heteroaryl," as used herein, means a mono- or multi-cyclic aromatic heterocycle which comprise at least one heteroatom such as nitrogen, sulfur and oxygen, but may include 1, 2, 3 or 4 heteroatoms. Aromatic groups also include fused polycyclic aromatic ring systems in which a carbocyclic aromatic ring or heteroaryl ring is fused to one or more other aromatic, heterocyclic or cycloalkyl ring. Examples include naphthyl, benzothienyl, benzofuranyl, indolyl, quinolinyl, benzothiazole, benzooxazole, benzimidazole, quinolinyl, isoquinolinyl and isoindolyl. Examples of suitable substituents on aromatic groups are as defined below.

The term "arylene" refers to an aryl group which is connected to the remainder of the molecule by two other bonds. By way of example, the structure of a 1,4-phenylene group is shown below:

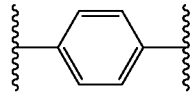

Examples of suitable substituents for an arylene group are as described below for an aryl group.

Non-aromatic heterocyclic rings are non-aromatic rings which include one or more heteroatoms such as nitrogen, oxygen or sulfur in the ring. The ring can be five, six, seven or eight-membered. Examples include tetrahydrofuranyl, tetrahyrothiophenyl, morpholino, thiomorpholino, pyrrolidinyl, piperazinyl, piperidinyl, and thiazolidinyl.

Suitable substituents on an aliphatic group (including cycloalkyl, an alkylene group or a hydrocarbyl group), non-aromatic heterocyclic group, benzylic or aryl group (carbocyclic and heteroaryl) are those which do not substantially interfere with the biological activity of the disclosed compounds. A substituent substantially interferes with biological activity when the biological activity is reduced by more than about 50% in a compound with the substituent compared with a compound without the substituent. Examples of suitable substituents include —R$^a$, —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NR$^c$COR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHNR$^a$R$^b$, —SO$_2$NH$_2$, —SO$_2$NHR$^a$, —SO$_2$NR$^a$R$^b$, —CH=CHR$^a$, —CH=CR$^a$R$^b$, —CRC=CR$^a$R$^b$, —CRC=CHR$^a$, —CR$^c$=CR$^a$R$^b$, —CCR$^a$, —SH, —SR$^a$, —S(O)R$^a$, —S(O)$_2$R$^a$. R$^a$-R$^d$ are each independently an alkyl group, aromatic group, non-aromatic heterocyclic group or —N(R$^a$R$^b$), taken together, form an optionally substituted non-aromatic heterocyclic group. The alkyl, aromatic and non-aromatic heterocyclic group represented by R$^a$-R$^d$ and the non-aromatic heterocyclic group represented by —N(R$^a$R$^b$) are each optionally and independently substituted with one or more groups represented by R$^\#$.

R$^\#$ is R$^+$, —OR$^+$, —O(haloalkyl), —SR$^+$, —NO$_2$, —CN, —NCS, —N(R$^+$)$_2$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)C(O)R$^+$, —C(O)CH$_2$C(O)R$^+$, —CO$_2$R$^+$, —C(O)R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)R$^+$, —NHSO$_2$N(R$^+$)$_2$, —NHSO$_2$R$^+$, —C(=S)N(R$^+$)$_2$, or —C(=NH)—N(R$^+$)$_2$.

R$^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine. Optionally, the group —N(R$^+$)$_2$ is a non-aromatic heterocyclic group, provided that non-aromatic heterocyclic groups represented by R$^+$ and —N(R$^+$)$_2$ that comprise a secondary ring amine are optionally acylated or alkylated.

Preferred substituents for a phenyl group, including phenyl groups represented by R$_1$-R$_4$, include C1-C4 alkyl, C1-C4 alkoxy, C1-C4 haloalkyl, C1-C4 haloalkoxy, phenyl, benzyl, pyridyl, —OH, —NH$_2$, —F, —Cl, —Br, —I, —NO$_2$ or —CN.

Preferred substituents for a cycloalkyl group, including cycloalkyl groups represented by R$_1$ and R$_2$, are alkyl groups, such as a methyl or ethyl groups.

In one embodiment, Y in Structural Formula I is a covalent bond, —C(R$_5$R$_6$)—, —(CH$_2$CH$_2$)—, trans-(CH=CH)—, cis-(CH=CH)— or —(C≡C)— group, preferably —C(R$_5$R$_6$)—. R$_1$-R$_4$ are as described above for Structural Formula I. R$_5$ and R$_6$ are each independently —H, an aliphatic or substituted aliphatic group, or R$_5$ is —H and R$_6$ is an optionally substituted aryl group, or, R$_5$ and R$_6$, taken together, are an optionally substituted C2-C6 alkylene group.

In specific embodiments, Y taken together with both >C=Z groups to which it is bonded, is an optionally substituted aromatic group. In this instance, certain bis(thio-hydrazide amides) are represented by Structural Formula II:

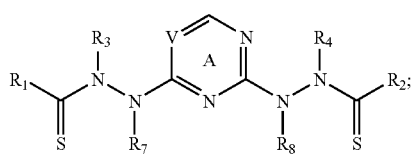

wherein Ring A is substituted or unsubstituted and V is —CH— or —N—. The other variables in Structural Formula II are as described herein for Structural Formula I or IIIa.

In particular embodiments, the bis(thio-hydrazide amides) are represented by Structural Formula IIIa:

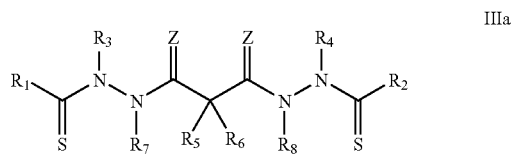

R$_1$-R$_8$ are as described above for Structural Formula I.

In Structural Formulas I-IIIa, R$_1$ and R$_2$ are the same or different and/or R$_3$ and R$_4$ are the same or different; preferably, R$_1$ and R$_2$ are the same and R$_3$ and R$_4$ are the same. In Structural Formulas I and IIIa, Z is preferably O. Typically in Structural Formulas I and IIIa, Z is O; R$_1$ and R$_2$ are the same; and R$_3$ and R$_4$ are the same. More preferably, Z is O; R$_1$ and R$_2$ are the same; R$_3$ and R$_4$ are the same, and R$_7$ and R$_8$ are the same.

In other embodiments, the bis(thio-hydrazide amides) are represented by Structural Formula IIIa: R$_1$ and R$_2$ are each an optionally substituted aryl group, preferably an optionally substituted phenyl group; R$_3$ and R$_4$ are each an optionally substituted aliphatic group, preferably an alkyl group, more preferably, methyl or ethyl; and R$_5$ and R$_6$ are as described above, but R$_5$ is preferably —H and R$_6$ is preferably —H, an aliphatic or substituted aliphatic group.

Alternatively, R$_1$ and R$_2$ are each an optionally substituted aryl group; R$_3$ and R$_4$ are each an optionally substituted aliphatic group; R$_5$ is —H; and R$_6$ is —H, an aliphatic or substituted aliphatic group. Preferably, R$_1$ and R$_2$ are each an optionally substituted aryl group; R$_3$ and R$_4$ are each an alkyl group; and R$_5$ is —H and R$_6$ is —H or methyl. Even more preferably, R$_1$ and R$_2$ are each an optionally substituted phenyl group; R$_3$ and R$_4$ are each methyl or ethyl; and R$_5$ is —H and R$_6$ is —H or methyl. Suitable substituents for an aryl group represented by R$_1$ and R$_2$ and an aliphatic group represented by R$_3$, R$_4$ and R$_6$ are as described below for aryl and aliphatic groups.

In another embodiment, the bis(thio-hydrazide amides) are represented by Structural Formula IIIa: R$_1$ and R$_2$ are each an optionally substituted aliphatic group, preferably a C3-C8 cycloalkyl group optionally substituted with at least one alkyl group, more preferably cyclopropyl or 1-methylcyclopropyl; R$_3$ and R$_4$ are as described above for Structural Formula I, preferably both an optionally substituted alkyl group; and R$_5$ and R$_6$ are as described above, but R$_5$ is preferably —H and R$_6$ is preferably —H, an aliphatic or substituted aliphatic group, more preferably —H or methyl.

Alternatively, the bis(thio-hydrazide amides) are represented by Structural Formula IIIa: R$_1$ and R$_2$ are each an optionally substituted aliphatic group; R$_3$ and R$_4$ are as described above for Structural Formula I, preferably both an optionally substituted alkyl group; and R$_5$ is —H and R$_6$ is —H or an optionally substituted aliphatic group. Preferably, R$_1$ and R$_2$ are both a C3-C8 cycloalkyl group optionally substituted with at least one alkyl group; R$_3$ and R$_4$ are both as described above for Structural Formula I, preferably an alkyl group; and R$_5$ is —H and R$_6$ is —H or an aliphatic or substituted aliphatic group. More preferably, R$_1$ and R$_2$ are both a C3-C8 cycloalkyl group optionally substituted with at least one alkyl group; R$_3$ and R$_4$ are both an alkyl group; and R$_5$ is —H and $R_6$ is —H or methyl. Even more preferably, $R_1$ and $R_2$ are both cyclopropyl or 1-methylcyclopropyl; $R_3$ and $R_4$ are both an alkyl group, preferably methyl or ethyl; and $R_5$ is —H and $R_6$ is —H or methyl.

In particular embodiments, the bis(thio-hydrazide amides) are represented by Structural Formula IIIb:

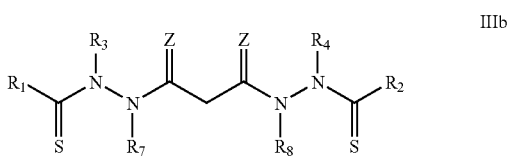

wherein $R_1$, $R_2$, $R_3$, $R_4$, $R_7$, $R_8$, and Z are as defined above for Structural Formula IIIa.

In specific embodiments, the bis(thio-hydrazide amides) are represented by Structural Formula IVa:

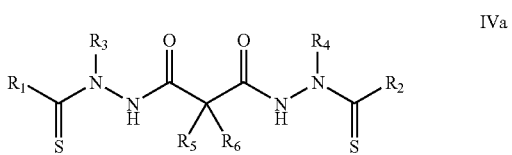

wherein: $R_1$ and $R_2$ are both phenyl, $R_3$ and $R_4$ are both methyl, and $R_5$ and $R_6$ are both —H; $R_1$ and $R_2$ are both phenyl, $R_3$ and $R_4$ are both ethyl, and $R_5$ and $R_6$ are both —H; $R_1$ and $R_2$ are both 4-cyanophenyl, $R_3$ and $R_4$ are both methyl, $R_5$ is methyl, and $R_6$ is —H; $R_1$ and $R_2$ are both 4-methoxyphenyl, $R_3$ and $R_4$ are both methyl, and $R_5$ and $R_6$ are both —H; $R_1$ and $R_2$ are both phenyl, $R_3$ and $R_4$ are both methyl, $R_5$ is methyl, and $R_6$ is —H; $R_1$ and $R_2$ are both phenyl, $R_3$ and $R_4$ are both ethyl, $R_5$ is methyl, and $R_6$ is —H; $R_1$ and $R_2$ are both 4-cyanophenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both 3-cyanophenyl, $R_3$ and $R_4$ are both methyl, and $R_5$ and $R_6$ are both —H; $R_1$ and $R_2$ are both 3-fluorophenyl, $R_3$ and $R_4$ are both methyl, and $R_5$ and $R_6$ are both —H; $R_1$ and $R_2$ are both 4-chlorophenyl, $R_3$ and $R_4$ are both methyl, $R_5$ is methyl, and $R_6$ is —H; $R_1$ and $R_2$ are both 2-dimethoxyphenyl, $R_3$ and $R_4$ are both methyl, and $R_5$ and $R_6$ are both —H; $R_1$ and $R_2$ are both 3-methoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, $R_5$ is methyl, and $R_6$ is —H; $R_1$ and $R_2$ are both 2,5-difluorophenyl, $R_3$ and $R_4$ are both methyl, and $R_5$ and $R_6$ are both —H; $R_1$ and $R_2$ are both 2,5-difluorophenyl, $R_3$ and $R_4$ are both methyl, $R_5$ is methyl, and $R_6$ is —H; $R_1$ and $R_2$ are both 2,5-dichlorophenyl, $R_3$ and $R_4$ are both methyl, and $R_5$ and $R_6$ are both —H; $R_1$ and $R_2$ are both 2,5-dimethylphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both phenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both cyclopropyl, $R_3$ and $R_4$ are both methyl, and $R_5$ and $R_6$ are both —H; $R_1$ and $R_2$ are both cyclopropyl, $R_3$ and $R_4$ are both ethyl, and $R_5$ and $R_6$ are both —H; $R_1$ and $R_2$ are both cyclopropyl, $R_3$ and $R_4$ are both methyl, $R_5$ is methyl, and $R_6$ is —H; $R_1$ and $R_2$ are both 1-methylcyclopropyl, $R_3$ and $R_4$ are both methyl, and $R_5$ and $R_6$ are both —H; $R_1$ and $R_2$ are both 1-methylcyclopropyl, $R_3$ and $R_4$ are both methyl, $R_5$ is methyl and $R_6$ is —H; $R_1$ and $R_2$ are both 1-methylcyclopropyl, $R_3$ and $R_4$ are both methyl, $R_5$ is ethyl, and $R_6$ is —H; $R_1$ and $R_2$ are both 1-methylcyclopropyl, $R_3$ and $R_4$ are both methyl, $R_5$ is n-propyl, and $R_6$ is —H; $R_1$ and $R_2$ are both 1-methylcyclopropyl, $R_3$ and $R_4$ are both methyl, and $R_5$ and $R_6$ are both methyl; $R_1$ and $R_2$ are both 1-methylcyclopropyl, $R_3$ and $R_4$ are both ethyl, and $R_5$ and $R_6$ are both —H; $R_1$ and $R_2$ are both 1-methylcyclopropyl, $R_3$ is methyl, $R_4$ is ethyl, and $R_5$ and $R_6$ are both —H; $R_1$ and $R_2$ are both 2-methylcyclopropyl, $R_3$ and $R_4$ are both methyl, and $R_5$ and $R_6$ are both —H; $R_1$ and $R_2$ are both 2-phenylcyclopropyl, $R_3$ and $R_4$ are both methyl, and $R_5$ and $R_6$ are both —H; $R_1$ and $R_2$ are both 1-phenylcyclopropyl, $R_3$ and $R_4$ are both methyl, and $R_5$ and $R_6$ are both —H; $R_1$ and $R_2$ are both cyclobutyl, $R_3$ and $R_4$ are both methyl, and $R_5$ and $R_6$ are both —H; $R_1$ and $R_2$ are both cyclopentyl, $R_3$ and $R_4$ are both methyl, and $R_5$ and $R_6$ are both —H; $R_1$ and $R_2$ are both cyclohexyl, $R_3$ and $R_4$ are both methyl, and $R_5$ and $R_6$ are both —H; $R_1$ and $R_2$ are both cyclohexyl, $R_3$ and $R_4$ are both phenyl, and $R_5$ and $R_6$ are both —H; $R_1$ and $R_2$ are both methyl, $R_3$ and $R_4$ are both methyl, and $R_5$ and $R_6$ are both —H; $R_1$ and $R_2$ are both methyl, $R_3$ and $R_4$ are both t-butyl, and $R_5$ and $R_6$ are both —H; $R_1$ and $R_2$ are both methyl, $R_3$ and $R_4$ are both phenyl, and $R_5$ and $R_6$ are both —H; $R_1$ and $R_2$ are both t-butyl, $R_3$ and $R_4$ are both methyl, and $R_5$ and $R_6$ are both —H; $R_1$ and $R_2$ are ethyl, $R_3$ and $R_4$ are both methyl, and $R_5$ and $R_6$ are both —H; or $R_1$ and $R_2$ are both n-propyl, $R_3$ and $R_4$ are both methyl, and $R_5$ and $R_6$ are both —H.

In particular embodiments, the bis(thio-hydrazide amides) are represented by Structural Formula IVb:

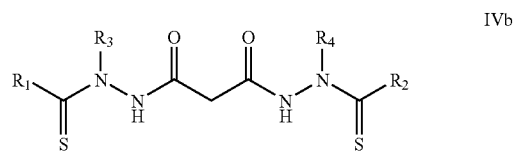

wherein $R_1$, $R_2$, $R_3$, and $R_4$ are as defined above for Structural Formula IVa.

In specific embodiments, the bis(thio-hydrazide amides) are represented by Structural Formula V:

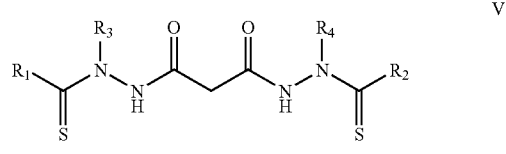

wherein: $R_1$ and $R_2$ are both phenyl, and $R_3$ and $R_4$ are both o-$CH_3$-phenyl; $R_1$ and $R_2$ are both o-$CH_3C(O)O$-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-$CF_3$-phenyl; $R_1$ and $R_2$ are both methyl, and $R_3$ and $R_4$ are both o-$CH_3$-phenyl; $R_1$ and $R_2$ are both —$(CH_2)_3$COOH; and $R_3$ and $R_4$ are both phenyl; $R_1$ and $R_2$ are both represented by the following structural formula:

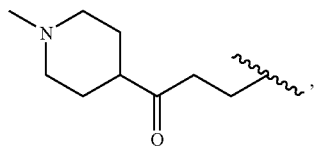

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl.

Preferred examples of bis(thio-hydrazide amides) include Compounds (1)-(18) and pharmaceutically acceptable salts and solvates thereof:

Compound (1)

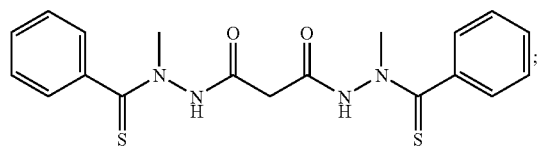

Compound (2)

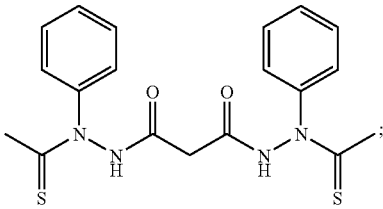

Compound (3)

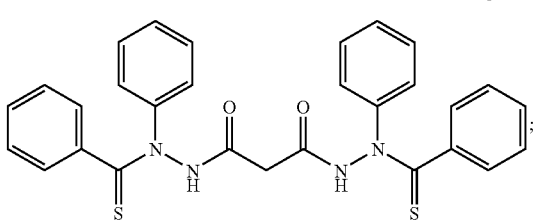

Compound (4)

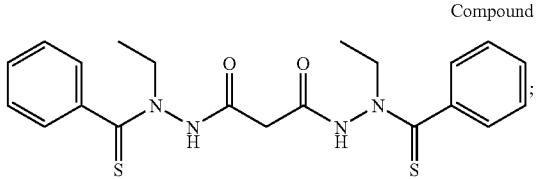

Compound (5)

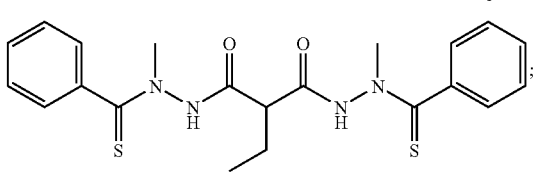

Compound (6)

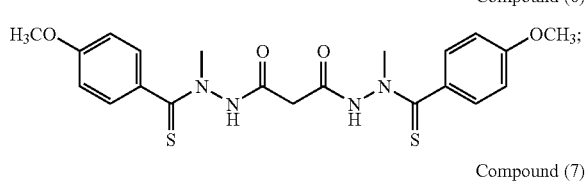

Compound (7)

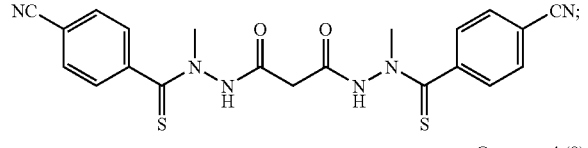

Compound (8)

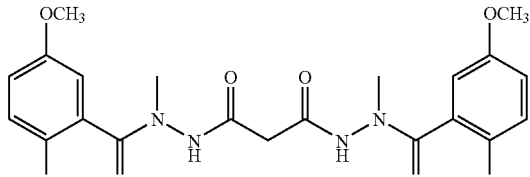

Compound (9)

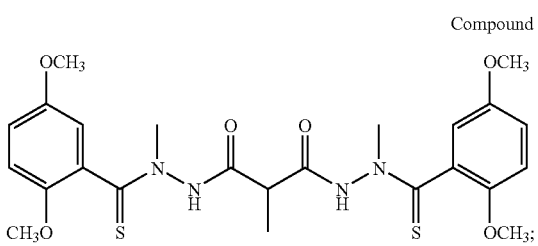

-continued

Compound (10)
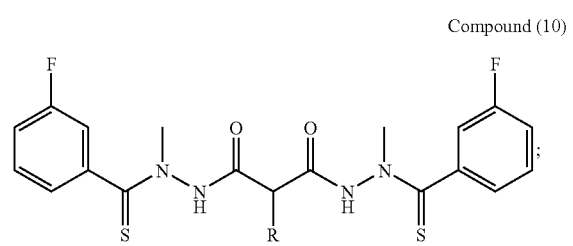

Compound (11)
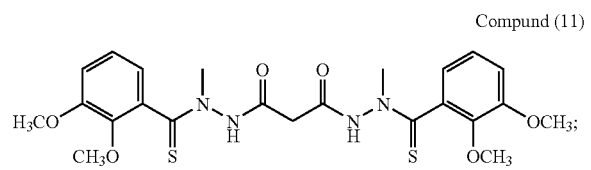

Compound (12)
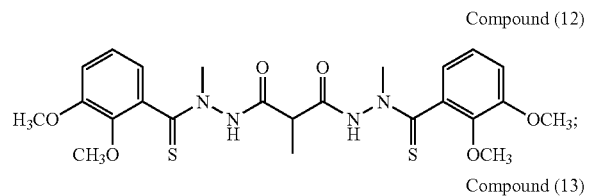

Compound (13)
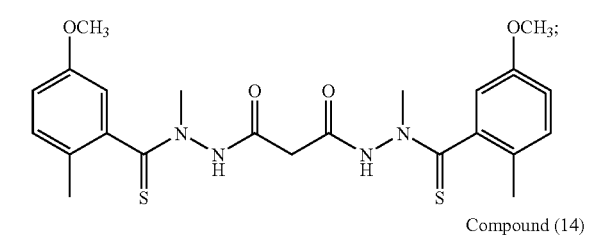

Compound (14)
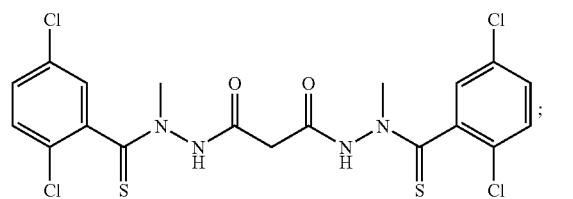

Compound (15)
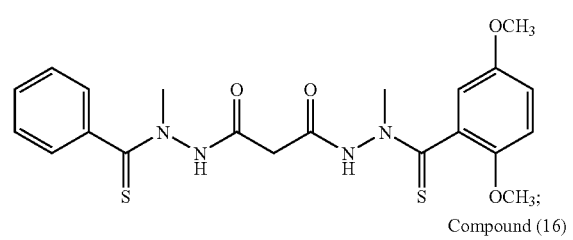

Compound (16)
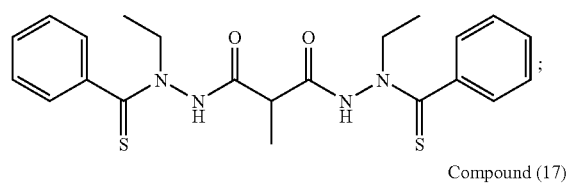

Compound (17)
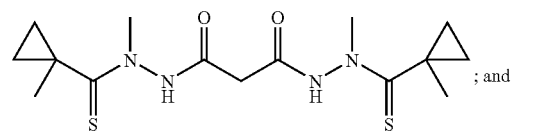
; and

Compound (18)
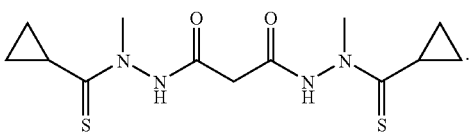

Especially preferred examples of bis(thio-hydrazide amides) include Compounds (1), (17), and (18) and pharmaceutically acceptable salts and solvates thereof.

As used herein, the term "bis(thio-hydrazide amides)" and references to the Structural Formulas of this invention also include pharmaceutically acceptable salts and solvates of these compounds and Structural Formulas.

As used herein, "Hsp70" includes each member of the family of heat shock proteins having a mass of about 70-kiloDaltons, including forms such as constituitive, cognate, cell-specific, glucose-regulated, inducible, etc. Examples of specific Hsp70 proteins include hsp70, hsp70hom; hsc70; Grp78/BiP; mt-hsp70/Grp75, and the like). Typically, the disclosed methods increase expression of inducible Hsp70. Functionally, the 70-kDa HSP (HSP70) family is a group of chaperones that assist in the folding, transport, and assembly of proteins in the cytoplasm, mitochondria, and endoplasmic reticulum. In humans, the Hsp70 family encompasses at least 11 genes encoding a group of highly related proteins. See, for example, Tavaria, et al., Cell Stress Chaperones, 1996; 1(1): 23-28; Todryk, et al., Immunology. 2003, 110(1): 1-9; and Georgopoulos and Welch, Annu Rev Cell Biol. 1993; 9:601-634; the entire teachings of these documents are incorporated herein by reference.

As used herein, an "Hsp70-responsive disorder" is a medical condition (specifically excluding cancer and cell proliferation/hyperproliferation disorders) wherein stressed cells can be treated by increased Hsp70 expression. Such disorders can be caused by a wide variety of cellular stressors, including, but not limited to Alzheimers' disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; autoimmune disease; infection (bacterial, viral, fungal, or parasitic); and the like.

In some embodiments, the Hsp70-responsive disorder is a neurodegenerative disorder. As used herein, a neurodegenerative disorder involves degradation of neurons such as cereberal, spinal, and peripheral neurons (e.g., at neuromuscular junctions), more typically degradation of cerebral and spinal neurons, or in preferred embodiments, degradation of cerebral neurons. Neurodegenerative disorders can include Alzheimers' disease; Huntington's disease; Parkinson's disease; spinal/bulbar muscular atrophy and other neuromuscular atrophies; and familial amyotrophic lateral sclerosis or other diseases associated with superoxide dismutase (SOD) mutations. Neurodegenerative disorders can also include degradation of neurons caused by ischemia, seizure, thermal stress, radiation, toxin exposure, infection, injury, and the like.

In some embodiments, the Hsp70-responsive disorder is a disorder of protein aggregation/misfolding, such as Alzheimers' disease; Huntington's disease; Parkinson's disease; and the like.

In another embodiment the Hsp70 responsive disorder is a treatment or condition which causes or may cause nerve damage. The compounds for use in the methods of the present invention can be used to reduce or prevent (inhibit the onset of) nerve damage (i.e., provide neuroprotection) in a subject i) suffering from a condition which causes or may cause nerve damage or ii) receiving treatment which causes or may cause nerve damage. In one aspect, the treatment which causes or may cause nerve damage is radiation therapy. In another aspect, the treatment is chemotherapy. In one aspect, the chemotherapy comprises administering an antimitotic agent (e.g. vincristine, vinorelbine, paclitaxel, or a paclitaxel analog). In one aspect, the chemotherapy comprises administering paclitaxel. In another aspect, the chemotherapy comprises administering a platinum derivative (e.g. cisplatinum, carboplatin, or oxaliplatin). In certain embodiments, the compounds for use in the methods of the present invention can be administered simultaneously as a combination therapy with the treatment which causes or may cause nerve damage. In other embodiments the compounds for use in the methods of the present invention can be administered before or after the treatment which causes may cause nerve damage. In certain embodiments the compounds for use in the methods of the present, invention can be administered between 30 minutes and 12 hours, between 1 hour and 6 before or after the treatment which causes or may cause nerve damage.

Nerve damage may be caused by a number of treatments including, but not limited to, radiation therapy; chemotherapy, e.g. cisplatinum, carboplatin, oxaliplatin, vincristine, vinblastine, vinorelbine, vindesine, ifosfamide, methotrexate, cladribine, altretamine, fludarabine, procarbazine, thiotepa, teniposide, arsenic trioxide, alemtuzumab, capecitabine, dacarbazine, denileukin diftitox, interferon alpha, liposomal daunorubicin, tretinoin, etoposide/VP-16, cytarabine, hexaamethylmelamine, suramin, paclitaxel, docetaxel, gemcitibine, thalidomide, and bortezomib; heart or blood pressure medications, e.g. amiodarone, hydralazine, digoxin, and perhxiline; medications to fight infection, e.g. metronidazole, nitrofurantoin, thalidomide, and INH; medications to treat skin conditions, e.g. dapsone; anticonvulsants, e.g. phenytoin; anti-alcohol medications, e.g. disulfiram; HIV medications, e.g. zidovudine, didanonsine, stavudine, zalcitabine, ritonavir, d4T, ddC, ddl, and amprenavir; cholesterol medications, e.g. lovastatin, pravastatin, indapamid, simvastatin, fluvastatin, atorvastatin, cerivastatin, and gemfibrozil; antirheumatics, e.g. chloroquine, cholchicine, organic gold, and penicillamine; nitrous oxide; lithium; and ergots.

In some embodiments, the Hsp70-responsive disorder is ischemia. Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like. In one preferred embodiment, the Hsp70-responsive disorder is cerebral or spinal ischemia. In another preferred embodiment, the Hsp70-responsive disorder is cardiac ischemia.

In various embodiments, the Hsp70-responsive disorder is seizure, e.g., eplileptic seizure, injury-induced seizure, chemically-induced seizure, and the like.

In some embodiments, the Hsp70-responsive disorder is due to thermal stress. Thermal stress includes hyperthermia (e.g., from fever, heat stroke, burns, and the like) and hypothermia. In a preferred embodiment the disorder is hyperthermia. In another preferred embodiment, the Hsp70-responsive disorder is burn trauma.

In preferred embodiments, the Hsp70-responsive disorder is atherosclerosis.

In various embodiments, the Hsp70-responsive disorder is radiation damage, e.g., due to visible light, ultraviolet light, microwaves, cosmic rays, alpha radiation, beta radiation, gamma radiation, X-rays, and the like. For example, the damage could be radiation damage to non-cancerous tissue in a subject treated for cancer by radiation therapy. In a preferred embodiment, the Hsp70-responsive disorder is radiation damage from visible light or ultraviolet light.

In various embodiments, the Hsp70-responsive disorder is mechanical injury, e.g., trauma from surgery, accidents, certain disease conditions (e.g., pressure damage in glaucoma) and the like. In a preferred embodiment, the Hsp70-responsive disorder is cerebral or spinal trauma. In another preferred embodiment, the Hsp70-responsive disorder is glaucoma (leading to pressure damage to retinal ganglions).

In various embodiments, the Hsp70-responsive disorder is exposure to a toxin. In preferred embodiments, the Hsp70-responsive disorder is exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

It has been found that the compounds described herein for use in the methods of the present invention also increase Natural Killer (NK) cell activity (see U.S. Provisional Application Patent Application No. 60/671,910, the entire contents of which are incorporated herein by reference). Increasing NK cell activity would also be beneficial for treating subjects with disorders including, but not limited to a neurodegenerative disorder. As used herein, a neurodegenerative disorder involves degradation of neurons such as cereberal, spinal, and peripheral neurons (e.g., at neuromuscular junctions), more typically degradation of cerebral and spinal neurons. Neurodegenerative disorders can include Alzheimers' disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; eplileptic seizure, injury-induced seizure, chemically-induced seizure, or other diseases associated with superoxide dismutase (SOD) mutations; and the like. Neurodegenerative disorders can also include degradation of neurons caused by ischemia, seizure, thermal stress, radiation, toxin exposure, infection, injury, and the like. Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like.

Other disorders in which increasing NK cell activity would be beneficial include disorders due to thermal stress, (thermal stress includes hyperthermia (e.g., from fever, heat stroke, burns, and the like) and hypothermia); radiation damage, e.g., due to visible light, ultraviolet light, microwaves, cosmic rays, alpha radiation, beta radiation, gamma radiation, X-rays, and the like, (for example, the damage could be radiation damage to non-cancerous tissue in a subject treated for cancer by radiation therapy); mechanical injury, e.g., trauma from surgery, accidents, certain disease conditions (e.g., pressure damage in glaucoma) and the like; and exposure to a toxin. e.g., exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

Thus is believed that the compounds disclosed herein for use in methods of the invention will be more efficient in treating the diseases described in the two paragraphs immediately above.

As used herein, the terms "treat", "treatment" and "treating" refer to administration of one or more therapies (e.g., one or more therapeutic agents such as the bis(thio-hydrazide amide)) to reduce, ameliorate, or prevent the progression, severity and/or duration of a Hsp70-responsive disorder, or to reduce, ameliorate, or prevent one or more symptoms (preferably, one or more discernible symptoms) of a Hsp70-responsive disorder In specific embodiments, the terms "treat", "treatment" and "treating" refer to the amelioration of at least one measurable physical parameter of a Hsp70-responsive disorder, not necessarily discernible by the patient. In other embodiments the terms "treat", "treatment" and "treating" refer to the inhibition of the progression of a Hsp70-responsive disorder, either physically by, e.g., stabilization of a discernible symptom, physiologically by, e.g., stabilization of a physical parameter, or both. In other embodiments the terms "treat", "treatment" and "treating" refer to the inhibition or reduction in the onset, development or progression of one or more symptoms associated with a Hsp70-responsive disorder.

As used herein, the terms "prevent", "prevention" and "preventing" refer to the prophylactic administration of one or more therapies (e.g., one or more therapeutic agents such as the bis(thio-hydrazide amide)) to reduce the risk of acquiring or developing a given Hsp70-responsive disorder, or to reduce or inhibit the recurrence, onset or development of one or more symptoms of a given Hsp70-responsive disorder. In a preferred embodiment, a compound of the invention is administered as a preventative measure to a patient, preferably a human, having a genetic or environmental risk factor for a Hsp70-responsive disorder.

As used herein, a "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein, an "effective amount" is the quantity of compound in which a beneficial clinical outcome is achieved when the compound is administered to a subject. A "beneficial clinical outcome" includes therapeutic or prophylactic treatment of stressed cells via increased expression of Hsp70 resulting in reduction or inhibition of cell degradation, a reduction in the severity of the symptoms associated with the cell degradation (e.g., reduction of Alzheimer's symptoms, prevention or treatment of reperfusion damage in ischemia, and the like). The amount of the bis(thio-hydrazide amide) or composition comprising the bis(thio-hydrazide amide) which will be effective in the prevention, treatment, management, or amelioration of a Hsp70-responsive disorder or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in Hardman, et al., eds., 1996, Goodman & Gilman's The Pharmacological Basis Of Basis Of Therapeutics $9^{th}$ Ed, McGraw-Hill, New York; Physician's Desk Reference (PDR) $57^{th}$ Ed., 2003, Medical Economics Co., Inc., Montvale, N.J., the entire teachings of which are incorporated herein by reference.

Exemplary doses of the bis(thio-hydrazide amide) include microgram to milligram amounts of the compound per kilogram of subject or sample weight (e.g., about 1 µg/kg to about 500 mg/kg, about 500 µg/kg to about 250 mg/kg, about 1 mg/kg to about 100 mg/kg, about 10 mg/kg to about 50 mg/kg, and the like).

The bis(thio-hydrazide amides) described herein can be administered to a subject by any conventional method of drug administration, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), rectally, vaginally, and the like. In specific embodiments, oral, parenteral, or local administration are preferred modes of administration for treatment of Hsp70-responsive disorders.

The bis(thio-hydrazide amides) described herein can be administered to the subject in conjunction with an acceptable pharmaceutical carrier or diluent as part of a pharmaceutical composition for treatment of Hsp70-responsive disorders. Formulation of the compound to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

In one embodiment, the method comprises topical administration. In such cases, the compounds may be formulated as a solution, gel, lotion, cream or ointment in a pharmaceutically acceptable form. Actual methods for preparing these, and other, topical pharmaceutical compositions are known or apparent to those skilled in the art and are described in detail in, for example, Remington's Pharmaceutical Sciences, $16^{th}$ and $18^{th}$ eds., Mack Publishing Company, Easton, Pa., 1980-1990).

Also included in the present invention are pharmaceutically acceptable salts of the bis(thio-hydrazide amides) described herein. These bis(thio-hydrazide amides) can have one or more sufficiently acidic protons that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

For example, pharmaceutically acceptable salts of the bis(thio-hydrazide amides) (e.g., those represented by Structural Formulas I-V or Compounds (1)-(18) are those formed by the reaction of the bis(thio-hydrazide amide) with one equivalent of a suitable base to form a monovalent salt (i.e., the compound has single negative charge that is balanced by a pharmaceutically acceptable counter cation, e.g., a monovalent cation) or with two equivalents of a suitable base to form a divalent salt (e.g., the compound has a two-electron negative charge that is balanced by two pharmaceutically acceptable counter cations, e.g., two pharmaceutically acceptable monovalent cations or a single pharmaceutically acceptable divalent cation). Divalent salts of the bis(thio-hydrazide amides) are preferred. "Pharmaceutically acceptable" means that the cation is suitable for administration to a subject. Examples include $Li^+$, $Na^+$, $K^+$, $Mg^{2+}$, $Ca^{2+}$ and $NR_4^+$, wherein each R is independently hydrogen, an optionally substituted aliphatic group (e.g., a hydroxyalkyl group, aminoalkyl group or ammoniumalkyl group) or optionally substituted aryl group, or two R groups, taken together, form an optionally substituted non-aromatic heterocyclic ring optionally fused to an aromatic ring. Generally, the pharmaceutically acceptable cation is $Li^+$, $Na^+$, $K^+$, $NH_3(C_2H_5OH)^+$ or $N(CH_3)_3(C_2H_5OH)^+$, and more typically, the salt is a disodium or dipotassium salt, preferably the disodium salt (see for example U.S. application Ser. No. 11/157,213, the entire contents of which are incorporated herein by reference).

Bis(thio-hydrazide amides) with a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

It will also be understood that certain compounds of the invention may be obtained as different stereoisomers (e.g., diastereomers and enantiomers) and that the invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

The compounds described herein and synthesis thereof were previously disclosed in Koya, et al.: U.S. Pat. Nos. 6,800,660, 6,924,312, and 6,762,204, U.S. application Ser. No. 10/807,919; Zhou et al. U.S. application Ser. No. 10/758,589 and Chen, et al., U.S. Pat. No. 6,825,235. The entire teachings of these documents are incorporated herein by reference.

EXEMPLIFICATION

The present invention is illustrated by the following examples, which are not intended to be limiting in any way.

Example 1

Bis (thiohydrazide) amides Are Distributed in Brain, Kidney, Liver, and Spleen; Compounds (1) and (18) Cross the Blood-Brain Barrier A study was designed to investigate the tissue distribution of compounds (1) and (18) (using atenolol as a negative control for distribution across the blood-brain barrier) in SW female mice, N=2 per group (total 4 groups including vehicle control. Reagents were obtained from Sigma, St Louis, Mo.; mice were obtained from Taconic Farms (Germantown N.Y.). The vehicle employed was 10% DMSO, 18% Cremophor RH40. The compounds were administered intravenously at a dose of 25 mg/kg. Blood was collected 30 min after administration, and tissue collection was performed immediately after blood collection. Plasma samples were prepared by combining 50 μL plasma+50 μL 1% dithiothreitol (DTT)+150 μL $CH_3CN$ (0.1% HCOOH), centrifuged at 10,000 rpm×5 min; 150 μL supernatant+90 μL $H_2O$. Tissue samples were prepared by homogenizing a weighed tissue sample in phosphor-buffered saline (PBS, ×1)+1% DTT (×1)+$CH_3CN$ (0.1% HCOOH) (×3)), centrifuged at 10,000 rpm×5 min; 150 μL supernatant+90 μL $H_2O$. 100 μL prepared samples were subjected to HPLC, using 5-95% $CH_3CN$ (0.1% HCOOH) as the eluent. The running time was 15 min. With this method, the retention times were 7.25 min for compound (18) and 7.99 min for compound (1).

FIG. 1 is a bar graph showing the concentrations of compound (1) and compound (18) in mouse plasma, brain, kidney, liver and spleen measured 30 min after injection in a first experiment. Compound (18) was detected in brain at a concentration of ~2 μM, which was ~7% of the plasma concentration, and compound (1) in brain was even higher, at ~27% of the concentration of compound (1) in plasma. Therefore, both compounds effectively cross the blood-brain barrier, with compound (1) achieving almost twice the concentration of compound (18) in the brain, and compound (1) achieving a concentration in the brain compared to plasma of 27% compared to the 7% achieved by compound (18). The concentrations in kidney, liver, and spleen 30 min after injection, were 50 μM, 33 μM, and 25 μM, respectively for Compound (18), and 28 μM, 32 μM, and 12 μM for compound (1). The distribution of compounds (18) and (1) in liver were similar, but the concentration of compound (18) was about twice that of compound (1) in kidney and spleen.

Figure 2:
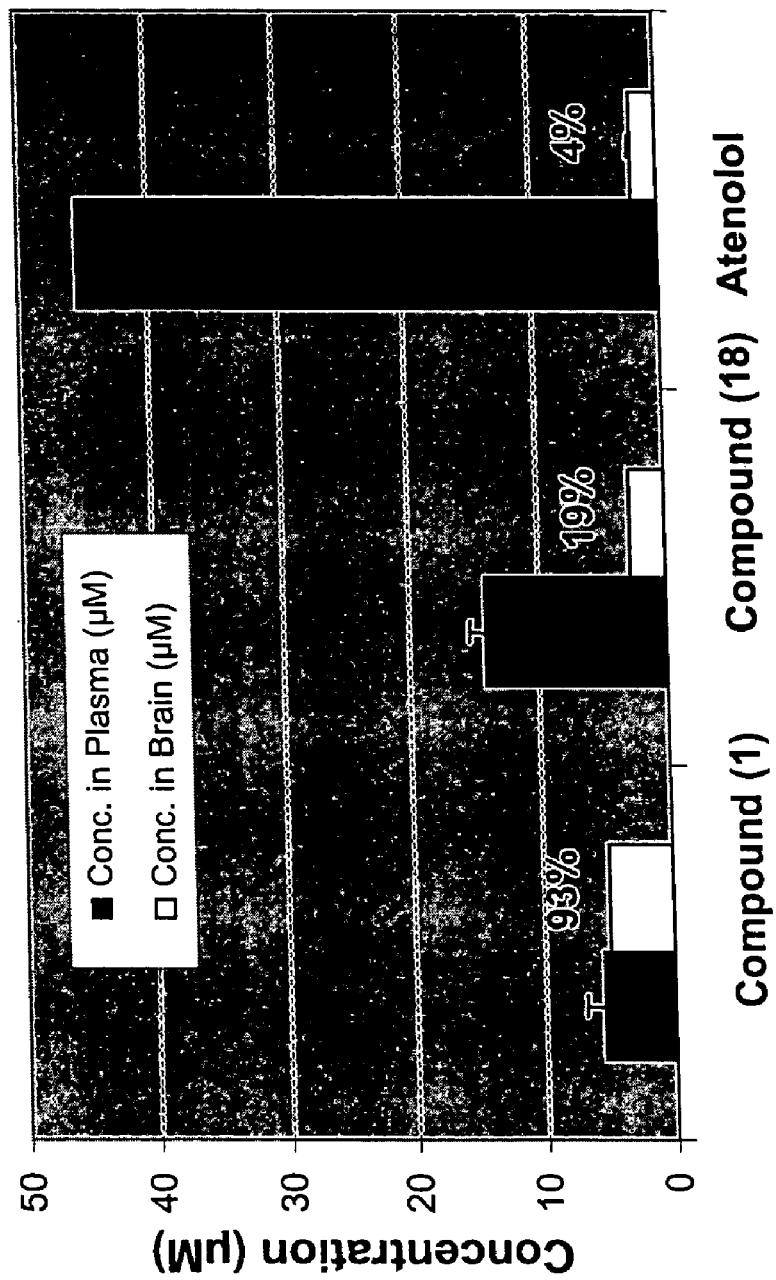
FIG. 2 is a bar graph showing the concentrations of compound (1) and compound (18) versus negative control atenolol in mouse plasma and brain.

A second experiment compared the compounds with a negative control (atenolol) for crossing the blood-brain barrier. FIG. 2 is a bar graph showing the concentrations of compound (1) and compound (18) versus negative control atenolol in mouse plasma and brain. Compound (1) and compound (18) achieve brain concentrations of 93% and 19% of plasma concentration, respectively, while negative control atenolol reaches only 4%. Thus, Compound (1) and compound (18) can cross the blood-brain barrier more effectively than atenolol.

Example 2

Compounds (1) and (9) have Excellent Bioavailibility

A study was designed to compare the tissue distribution and bioavailability of compounds (1) and (9) in SW female mice. The compounds were prepared in two formulations: Formulation A contained 10% DMSO, and 18% Cremophor RH40 in water; Formulation B contained ethanol:Cremophor EL in a 1:1 ratio. The formulations were administered according to the following distribution (N=4): Group 1: intravenous: 25 mg/kg compound (1) in formulation A; Group 2: per os: 100 mg/kg compound (1) in formulation B; Group 3: intravenous: 25 mg/kg compound (9) in formulation A; Group 4: per os: 100 mg/kg compound (9) in formulation B.

Blood samples were taken at 30 min, 1, 2, and 4 hr after injection. Brain tissue samples were taken after blood collected at 30 min, where one mouse from each group was selected and its brain was removed for analysis.

Blood samples were combined with 3-5 mg solid DTT, after which the sample was vortexed and centrifuged at 6,000 rpm×10 min. A 50 µL aliqot of plasma was taken, followed by the addition of 50 µL 1% DTT and 150 µL $CH_3CN$ (0.1% TFA). The mixture was vortexed and centrifuged at 10,000 rpm×5 min. The 150 µL supernatant was diluted with 150 µL water. A weighed tissue sample was homogenized in PBS (1:1), then combined with 1% DTT (1:1), followed by the addition of $CH_3CN$ containing 0.1% TFA (3:1). The mixture was vortexed and centrifuged at 10,000 rpm×5 min. The 150 µL supernatant was diluted with 150 µL water. 100 µL prepared samples were subjected to HPLC, using 5-95% $CH_3CN$ (0.1% trifluoroacetic acid) as the eluent.

Figure 3:
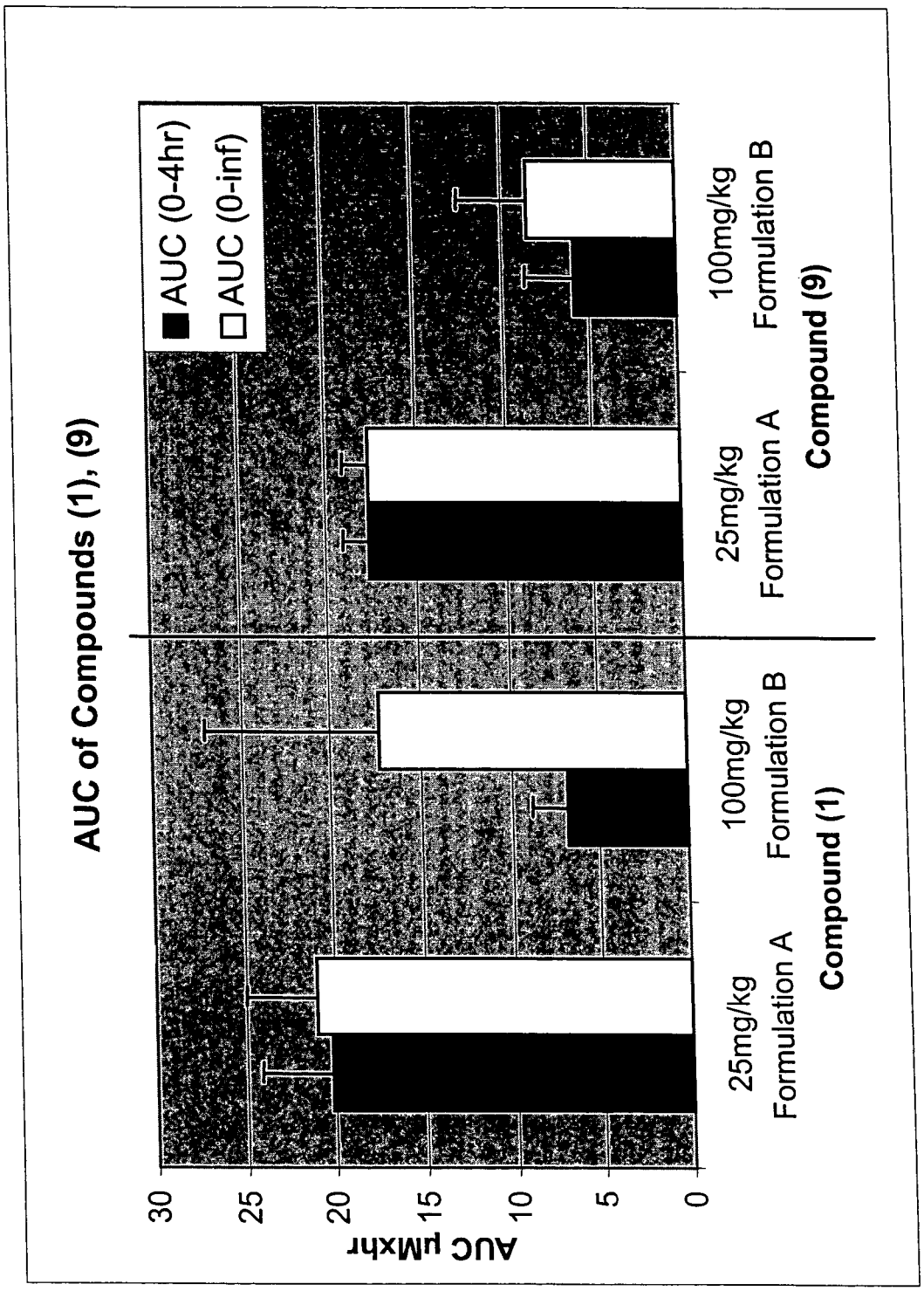
FIG. 3 is a bar graph showing the AUC (area under the curve) values (in μM×hour) for compound (1) and compound (9) in mouse plasma and brain from 0-4 hours and from 0-extrapolated to infinity.
Figure 4:
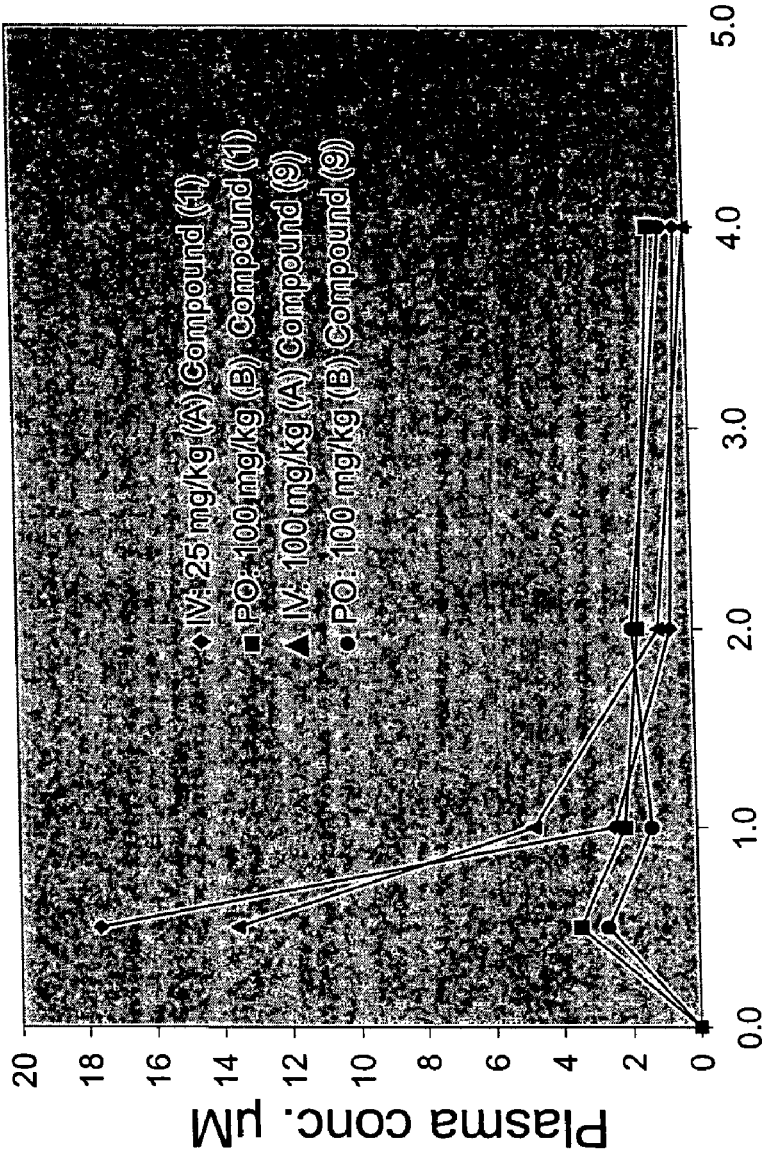
FIG. 4 is a graph showing mouse plasma concentration versus time for compound (1) and compound (9).
Figure 5:
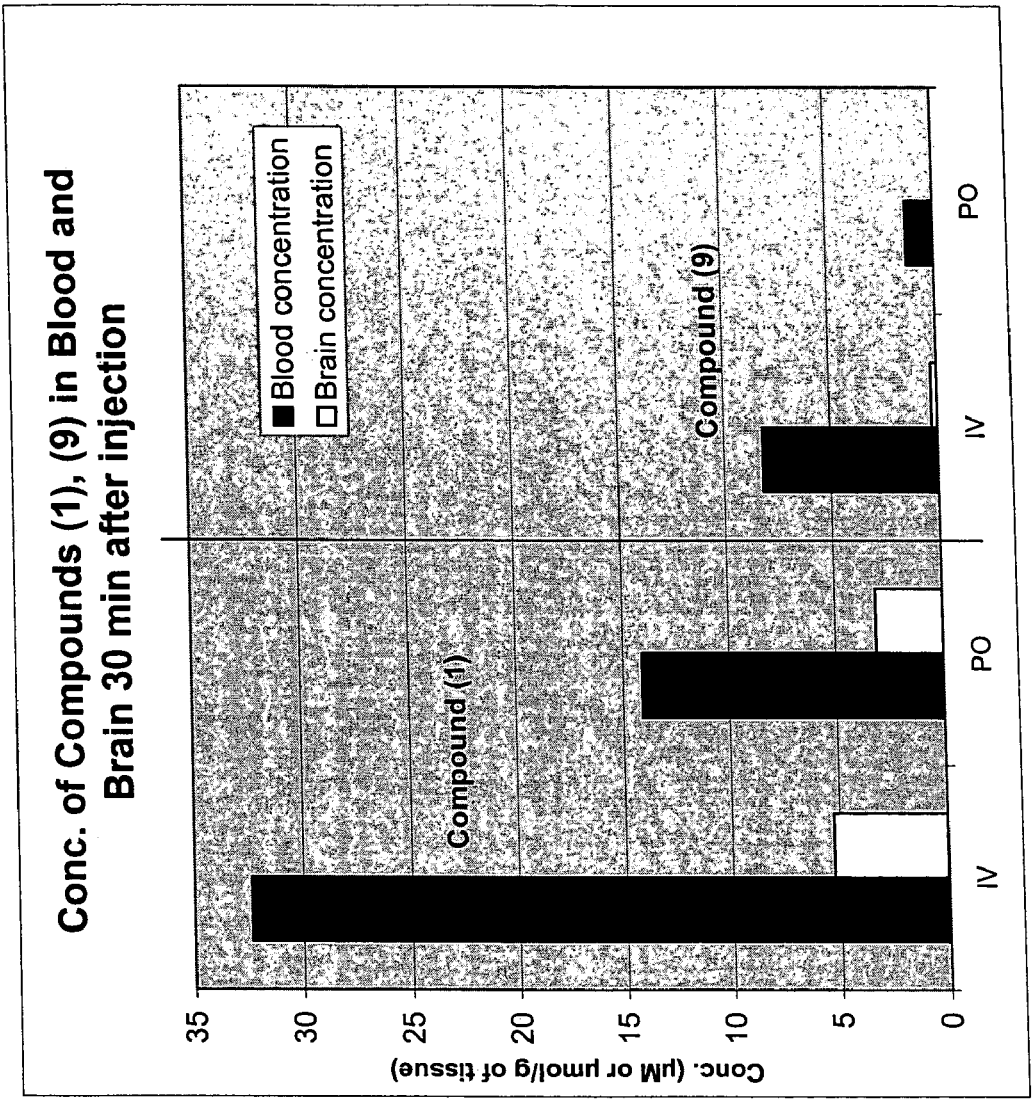
FIG. 5 is a bar graph showing the concentration of compound (1) and compound (9) in mouse brain 30 minutes after administration.

FIGS. 3-5 shows the distribution of compounds (1) and (9) versus various parameters.

FIG. 3 is a bar graph showing the AUC (area under the curve) values (in µM×hour) for compound (1) and compound (9) in mouse plasma and brain from 0-4 hours and from 0-extrapolated to infinity. The 4 hour vs infinity AUC values for intravenous administration of compound (1) by formulation A were nearly identical, as well as for compound (9). For per os administration using formula B, compound (1) reached about 30% of the intravenous value at 4 hours and about 80% of the intravenous value at infinity. Compound (9) under per os administration using formula B reached about 30% of the intravenous value at 4 hours but only about 50% of the intravenous value at infinity.

FIG. 4 is a graph showing mouse plasma concentration versus time for compound (1) and compound (9). The half life of both compounds (1) and (9) by per os administration with formulation B were much longer than by intravenous injection. The half life of compound (1) in formulation B (2.3 hr) was slightly shorter than that of compound (9) (3.8 hr). The bioavailabilities of compounds (1) and (9) were similar (~8%).

FIG. 5 is a bar graph showing the concentration of compound (1) and compound (9) in mouse brain 30 minutes after administration. Compound (1) was detected in brain at 30 min in significant concentrations (5.25 µmol/g (iv) and 3.09 µmol/g (po) of tissue) compared to compound (9) at 30 min after both IV and PO injections. Therefore, compound (1) crosses the blood-brain barrier more effectively than compound (9).

Example 3

Bis(thio-hydrazide amides) Induce Hsp70 in Normal Cells

Non-tumor-bearing mice were with either vehicle alone or compound (1). The vehicle employed was 10% DMSO, 18% Cremophor RH40. Compound (1) was combined with vehicle (2.5 mg/mL) and administered intravenously (25 mg/kg) 3 times a week. Plasma samples were prepared from tail bleed. Plasma Hsp70 levels were determined by Enzyme-Linked Immunosorbent Assay (ELISA).

Figure 6:
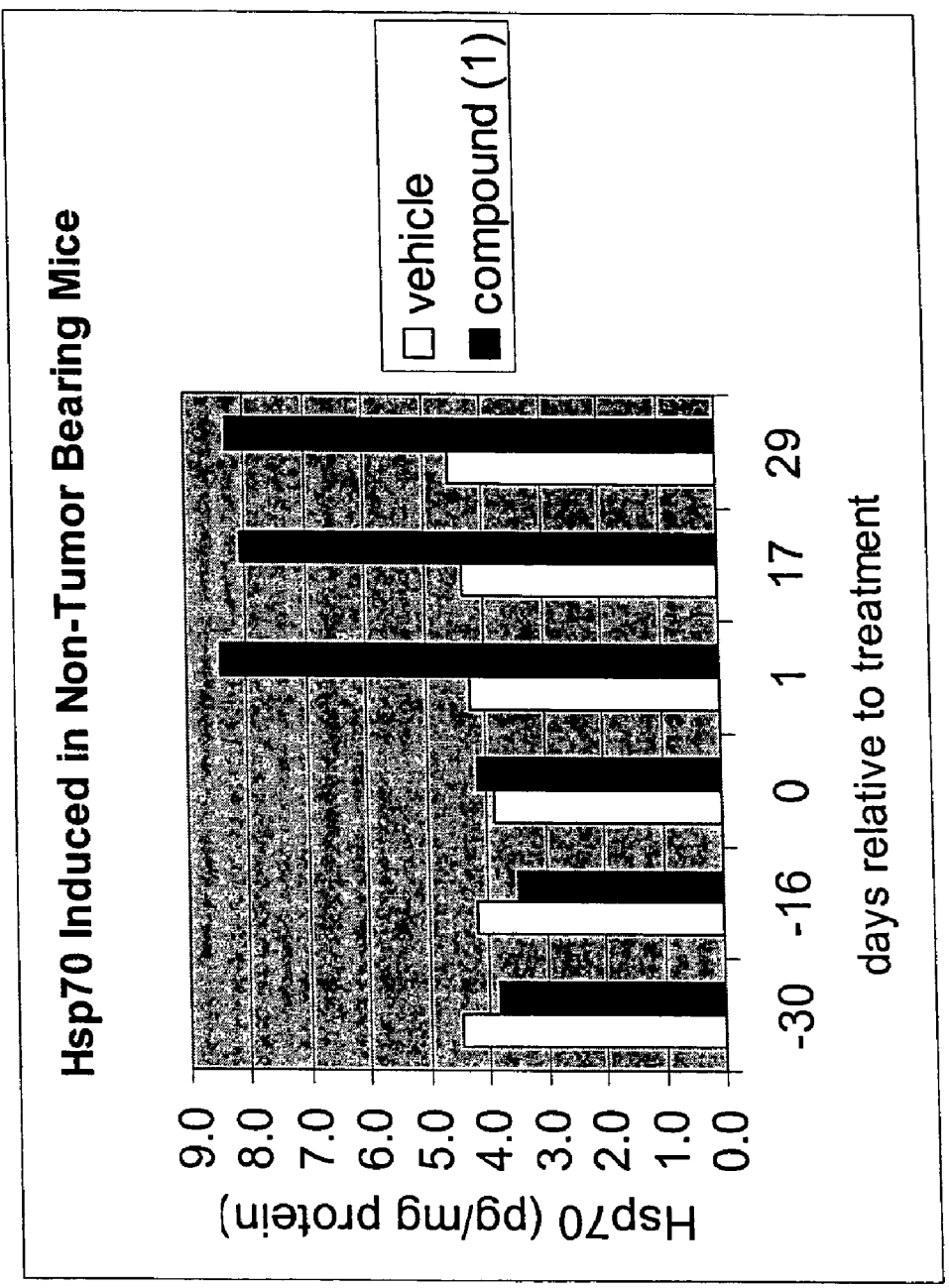
FIG. 6 is a bar graph showing the increase in plasma levels of Hsp70 in normal (non-tumor bearing) mice upon administration of compound (1).

FIG. 6 is a bar graph showing the increase in plasma levels of Hsp70 in normal (non-tumor bearing) mice upon administration of compound (1) compared to vehicle. Thus, this demonstrates that the bis(thio-hydrazide amides), administered alone, can induce Hsp70 in normal cells.

Examples 4-8

Heat shock proteins (Hsp) are induced under a variety of stress conditions and bind to other proteins to prevent their denaturation. Hsps can protect the cell from apoptotic death. Agents that induce the production of Hsp70 can have protective activity against a wide range of insults, and may have particular utility in neurological disorders. The neuroprotectant activity of Hsp70 inducing bis(thio-hydrazide amides) can be assessed in a variety of animal neurological disease models. Specifically, animal models of stroke, amyotrophic lateral sclerosis, Huntington's disease, Parkinson's disease, and Alzheimer's disease are appropriate settings for testing efficacy. Some example animal models are provided below.

Example 4

Cerebral Ischemia (Stroke)

The benefit of the disclosed treatment with Hsp70 inducing bis(thio-hydrazide amides) can be assessed in rodent models of stroke. For example the stroke model described in Longa, et al. (Longa, E. Z., Weinstein, P. R., Carlson, S., and Cummins, R. (1989) Reversible middle cerebral artery occlusion without craniectomy in rats. Stroke 20:84-91) can be utilized.

Rats are anesthetized with ketamine, and then infarction is induced by extracranial vascular occlusion. A 4-0 nylon intraluminal suture is placed into the cervical internal carotid artery and is advanced intracranially to block blood flow into the middle cerebral artery. Collateral blood flow is reduced by interrupting all branches of the external carotid artery and all extracranial branches of the internal carotid artery. A bis (thiohydrazide) amide, e.g., compound (1), can be dosed just prior to or just after induction of the infarction. The dose may be, for example, 10 to 100 mg/kg body weight administered once per week, three times per week, or daily by any conventional mode of administration, e.g., orally or intravenously. Neurologic deficit, mortality, gross pathology (infarction size), and histochemical staining can be analyzed to assess efficacy of the compounds. Since this is a very acute model, and death is often observed by three days after infarction, the modeling may consist of only a single administration of drug.

Example 5

Familial Amyotrophic Lateral Sclerosis (ALS)

The efficacy of compounds in the treatment of ALS can be modeled using the SOD1 transgenic mouse model (Gurney, M. E., Pu, H., Chiu, A. Y., Dal Canto, M. C., Polchow, C. Y., Alexander, D. D., Caliendo, J., Hentati, A., Kwon, Y. W., and Deng, H. X. (1994) Motor neuron degeneration in mice that express a human CuZn superoxide dismutase mutation. *Science* 264:1772-1775). Mutations of human CuZn superoxide dismutase (SOD) are found in patients with familial ALS. Expression of the human SOD gene containing a substitution of glycine-to-alanine at amino acid 93 leads to motor neuron disease in transgenic mice. As a result of motor neuron loss from the spinal cord, the mice became paralyzed and die by 5 to 6 months of age.

To test the efficacy of the Hsp70 inducing bis(thio-hydrazide amides), transgenic mice having the SOD1 mutation (SOD1$^{G93A}$) are treated with the compounds, and the effect on disease is monitored. The symptoms are clinically apparent in these animals at 2.5 to 3 months of age. Compounds can be dosed starting at this time. The dose may be, for example, 10 to 100 mg/kg body weight administered once per week or three times per week by the oral or intravenous route. Endpoints include functional impairment of motor function as well as histological changes. The latter endpoints include histopathology of brain and spinal cord assessing degeneration of motor neurons and the appearance of neurofilament-rich inclusions in spinal motor neurons. If long-term administration is performed, the impact on mouse survival can be assessed.

Example 6

Huntington's Disease (HD)

A transgenic mouse model of HD exists, allowing the testing of Hsp70 inducing bis(thio-hydrazide amides) for efficacy in this disease setting (Mangiarini, L., Sathasivam, K., Seller, M., Cozens, B., Harper, A., Hetherington, C., Lawton, M., Trottier, Y., Lehrach, H., Davies, S. W., and Bates, G. P. (1996) Exon 1 of the HD gene with an expanded CAG repeat is sufficient to cause a progressive neurological phenotype in transgenic mice. *Cell* 87:493-506; Carter, R. J., Lione, L. A., Humby, T., Mangiarini, L., Mahal, A., Bates, G. P., Dunnett, S. B., and Morton, A. J. (1999) Characterization of progressive motor deficits in mice transgenic for the human Huntington's disease mutation. *J. Neuroscience* 19:3248-3257). HD is caused by a CAG/polyglutamine repeat expansion. These transgenic mice (R6/2 transgenics) have the 5' end of the human HD gene with (CAG)115-(CAG)150 repeat expansions. The mice exhibit progressive neurological pathologies similar to HD, including abnormal and involuntary movements, tremors, and epileptic seizures.

These transgenic mice show overt behavioral changes at approximately 8 weeks of age. As early as 5 to 6 weeks of age, they display more subtle deficiencies in motor skills. Hsp70 inducing bis(thio-hydrazide amides), e.g., compound (1), can be administered by intravenous or oral administration at doses of 10-100 mg per kg of body weight starting at various times (for example, at 5 to 6 weeks of age). Compounds can be given on multiple different dosing schedules (e.g., once per week versus three times per week). Performance on one or more rodent motor tests such as swimming tank, beam walking, rotarod apparatus, and footprint test (see Carter, et al., 1999) can be performed to assess the activity of the compounds in preventing loss of neurological function in HD mice.

Example 7

Parkinson's Disease (PD)

There are two widely employed models of PD in which disease is induced by chemical treatment. These are the 6-OHDA (Zigmond, M. J. and Stricker, E. M. (1984) Parkinson's disease: studies with an animal model. *Life Sci.* 35:5-18; Sauer, H. and Oertel, W. H. (1994) Progressive degeneration of nigrostriatal dopamine neurons following intrastriatal terminal lesions with 6-hydroxydopamine: a combined retrograde tracing and immunocytochemical study in the rat. *Neuroscience* 59:401-415) and the MPTP (Langston, J. W., Forno, L. S., Rebert, C. S., and Irwin, I. (1984) Selective nigral toxicity after systemic administration of 1-methyl-4-phenyl-1,2,5,6-tetrahydropyrine (MPTP) in the squirrel monkey. *Brain Res.* 292:390-4) models. An example of a test of Hsp70 inducing bis(thio-hydrazide amides), e.g., compound (1), using the 6-OHDA is described.

Young adult male rats are injected with Fluoro-Gold (FG) by stereotactic injection into the striatum in the brain in order to facilitate visualization of the neurons in the substantia nigra, the site of PD. Under anesthesia, 0.2 μl of a 4% solution of FG is administered by stereotactic injection (1 mm anterior from bregma, 3 mm lateral, and 4.5 mm ventral from dura into both striata). One week after FG injection, the rats receive a stereotactic injection of 6-OHDA (20 μg dissolved in 4 μl saline; Sigma) into the striatum on one side of the brain, at the same coordinates as the FG injection. Hsp70 inducing bis(thio-hydrazide amides), e.g., compound (1), can be administered by intravenous or oral administration at doses of 10-100 mg per kg of body weight. The compounds can be given at the time of 6-OHDA injection or some time (2-4 weeks, for example) subsequent to 6-OHDA treatment. Rats are sacrificed 8 and 16 weeks after 6-OHDA injection. The endpoints of this model are 1) behavioral changes as monitored in-life at various times by assessment of turning (rotational) behavior using classical neurological read-out, and 2) the brain is removed after sacrifice, thin sections are made using a cryostat, and immunohistochemistry is performed as described in Zigmond and Stricker (1984). Efficacy of the Hsp70 inducing bis(thio-hydrazide amides) is demonstrated by a decrease in rotational behavior as well as a reduction in the loss of nigral dopaminergic neurons.

Example 8

Alzheimer's Disease (AD)

There are several transgenic mouse models of AD. One such model that is widely used to test the efficacy of drugs in AD was described by Holcomb, et al. (Holcomb, L., Gordon, M. N., McGowan, E., Yu, X., Benkovic, S., Jantzen, P., Wright, K., Saad, I., Mueller, R., Morgan, D., Sanders, S., Zehr, C., O'Campo, K., Hardy, J., Prada, C. M., Eckman, C., Younkin, S., Hsiao, K., and Duff, K. (1998) Accelerated Alzheimer-type phenotype in transgenic mice carrying both mutant amyloid precursor protein and presenilin 1 transgenes. *Nature Medicine* 4:97-100). This model contains two different genes associated with AD. One is a mutation in the amyloid precursor protein (APP). The mutant APP (K670N, M671L) transgenic line, Tg2576, has elevated amyloid beta-protein levels at an early age, and, later, develops extracellular AD-type A beta deposits in the brain. The other gene is a mutated presenilin-1 (PS1) gene. The doubly transgenic progeny from a cross between Tg2576 and the PS1 mutant PS1M146L transgenic line develop large numbers of fibrillar A beta deposits in cerebral cortex and hippocampus far earlier than their singly transgenic Tg2576 mice.

Hsp70 inducing bis(thio-hydrazide amides), e.g., compound (1), can be dosed in mice at various times. The age of mice at the start of drug dosing may be varied. For example, a treatment starting time may be at 3 months of age, a time at which the brain deposits are first detectable. The dose may be, for example, 10 to 100 mg/kg body weight administered once per week or three times per week by the oral or intravenous route. The effect of drug treatment can be assessed by measuring AD-type deposits in the brain as well as by assessing function of the mice in a maze test.

Example 9

Measurement of Heat Shock Protein 70 (Hsp70)

Plasma Hsp70 was measured by a sandwich ELISA kit (Stressgen Bioreagents Victoria, British Columbia, CANADA) according to a modified protocol in house. In brief, Hsp70 in plasma specimens and serial concentrations of Hsp70 standard were captured onto 96-well plate on which anti-Hsp70 antibody was coated. Then captured Hsp70 was detected with a biotinylated anti-Hsp70 antibody followed by incubation with europium-conjugated streptavidin. After each incubation unbound materials were removed by washing. Finally, antibody-Hsp70 complex was measured by time resolved fluorometry of europium. Concentration of Hsp70 was calculated from a standard curve.

Example 10

Measurement of Natural Killer Cell Cytotoxic Activity

The following procedure can be employed to assay NK cell activity in a subject. The procedure is adapted from Kantakamalakul W, Jaroenpool J, Pattanapanyasat K. A novel enhanced green fluorescent protein (EGFP)-K562 flow cytometric method for measuring natural killer (NK) cell cytotoxic activity. J Immunol Methods. 2003 Jan. 15; 272:189-197, the entire teachings of which are incorporated herein by reference.

Materials and methods: Human erythroleukaemic cell line, K562, was obtained from American Type Culture Collection (CCL-243, American Type Culture Collection, Manassas, Va.), and cultured in RPMI-1640 medium (Cat#11875-093Gibco Invitrogen Corp, Carlsbad, Calif.) supplemented with 10% heat inactivated fetal calf serum (Gibco), 2 mM L-glutamine, 100 µg/ml streptomycin and 100 IU/ml penicillin at 37° C. with 5% $CO_2$. K562 cells were transduced with retroviral vector which encode green fluorescent protein (eGFP). Stable cell line was selected with antibiotic, G418. About 99.6% G418 resistant cells were eGFP positive after section.

The subject's peripheral blood mononuclear cells (PBMCs) were prepared by clinical study sites and received in BD Vacutainer Cell Preparation Tube with sodium heparin (Product Number: 362753, Becton Dickinson, Franklin Lakes, N.J.).

Two-fold serial dilution of 800 µL effector cells (patient's PBMC) starting at concentration of $1\times10^6$ cells/mL were put into four individual polystyrene 12×75-mm tubes. Log phase growing target cells (K562/eGFP) were adjusted with growth medium (RPMI-1640) to a concentration of $1\times10^5$ cells/mL and 100 µL targets then added into the tubes to provide effector/target (E/T) ratios of 80:1, 40:1, 20:1, 10:1. Effector cells alone and target cells alone were used as controls. All tubes were incubated at 37° C. with 5% $CO_2$ for about 3.5 hr. Ten microliters of propidium iodide (PI) at a concentration of 1 mg/mL was added t each tube including effector and target control tubes and then incubated at room temperature for 15 min.

Cytotoxic activity was analyzed with a FACSCalibur flow cytometer (Becton Dickinson). Linear amplification of the forward and side scatter (FSC/SSC) signals, as well as logarithmic amplification of eGFP and PI emission in green and red fluorescence were obtained. Ten thousand events per sample tube with no gating for acquisition were collected for analysis. Data analysis for two-parameter dot plots for eGFP versus PI was performed using CELLQuest (Becton Dickinson Biosciences) software to enumerate live and dead target cells. Debris and dead cells were excluded by setting a threshold of forward light scatter.

Example 11

Combination Therapy Induces Hsp70

A Phase I trial was conducted for combined administration of a bis(thio-hydrazide) amide (Compound (1)) and a taxane (paclitaxel) to human subjects with various advanced solid tumors. Compound (1) and paclitaxel were co-administered intravenously over 3 hours every 3 weeks. Starting doses were 44 milligrams/meter$^2$ (mg/m$^2$, or 110 micromoles/meter$^2$ (µmol/m$^2$)) Compound (1) and 135 mg/m$^2$ (158 µmol/m$^2$) paclitaxel. Paclitaxel was then increased to 175 mg/m$^2$ (205 µmol/m$^2$), followed by escalation of Compound (1) to establish the maximum tolerated dose based on first cycle toxicity in 3 to 6 patients at each dose level. Pharmacokinetic (PK) studies were performed during cycle 1 using liquid chromatography/mass spectrometry (LC/MS) to measure both compounds in plasma. Heat shock protein 70 (Hsp70) was measured in plasma before and after treatment. 35 patients were evaluated at 8 dose levels, including paclitaxel at 135 mg/m$^2$ (158 µmol/m$^2$) and Compound (1) at 44 mg/m$^2$, and paclitaxel at 175 mg/m$^2$ (205 µmol/m$^2$) and Compound (1) at a doses ranging among 44-525 mg/m$^2$ (110-1311 µmol/m$^2$). Table 1 shows the eight different doses #1-#8 in mg/m$^2$ and µmol/m$^2$.

TABLE 1

|  | #1 | #2 | #3 | #4 | #5 | #6 | #7 | #8 |
|---|---|---|---|---|---|---|---|---|
| Compound (1), mg/m$^2$ | 44 | 44 | 88 | 175 | 263 | 350 | 438 | 525 |
| Compound (1), µmol/m$^2$ | 110 | 110 | 220 | 437 | 657 | 874 | 1094 | 1311 |
| Paclitaxel, mg/m$^2$ | 135 | 175 | 175 | 175 | 175 | 175 | 175 | 175 |
| Paclitaxel, µmol/m$^2$ | 158 | 205 | 205 | 205 | 205 | 205 | 205 | 205 |

No serious effects specifically attributable to Compound (1) were observed. Paclitaxel dose limiting toxicities occurred in a single patient in each of the top three dose levels (neutropenia, arthralgia, and febrile neutropenia with mucositis) resulting in cohort expansion. Compound (1) exhibited linear PK that was unaffected by paclitaxel dose, and was rapidly eliminated from plasma with terminal-phase half life of 0.94±0.23 hours (h) and total body clearance of 28±8 Liters/hour/meter² (L/h/m²). Its apparent volume of distribution was comparable to total body water ($V_{ss}$ 23±16 L/m²). Paclitaxel PK appeared to be moderately dependent on the Compound (1) dose, as indicated by a significant trend toward decreasing clearance, and increase in peak plasma concentration and $V_{ss}$, but without affecting the terminal phase half-life. These observations are consistent with competitive inhibition of paclitaxel hepatic metabolism. Increased toxicity at higher dose levels was consistent with a moderate increase in systemic exposure to paclitaxel. Induction of Hsp70 protein in plasma was dose dependent, peaking between about 8 hours to about 24 hours after dosing.

Figure 7A:
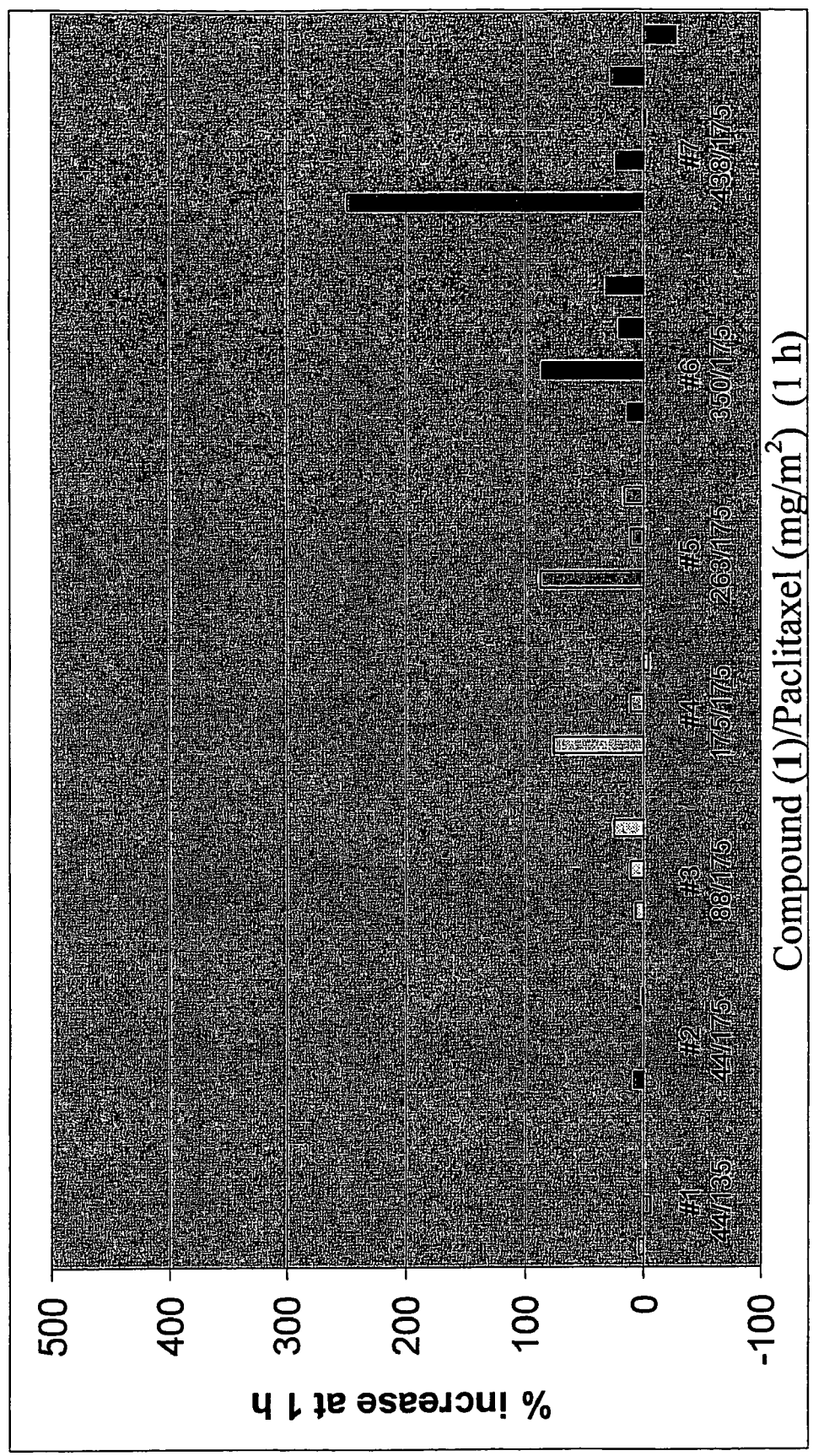
FIGS. 7A, 7B, and 7C are bar graphs showing the percent increase in Hsp70 plasma levels associated with administration of the Compound (1)/paclitaxel combination therapy at 1 hour (FIG. 7A), 5 hours (FIG. 7B), and 8 hours (FIG. 7C) after administration.
Figure 7B:
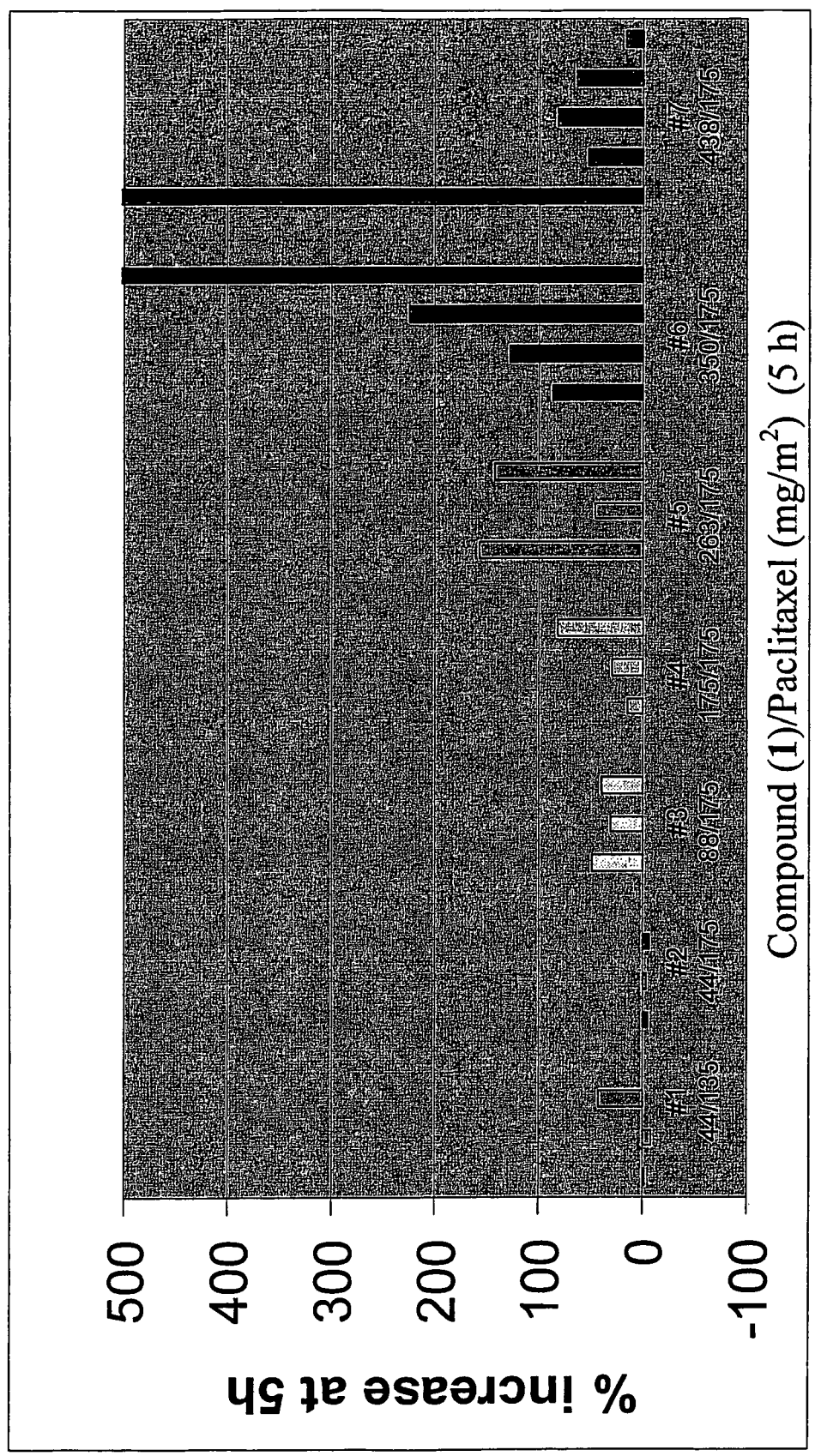
Figure 7C:
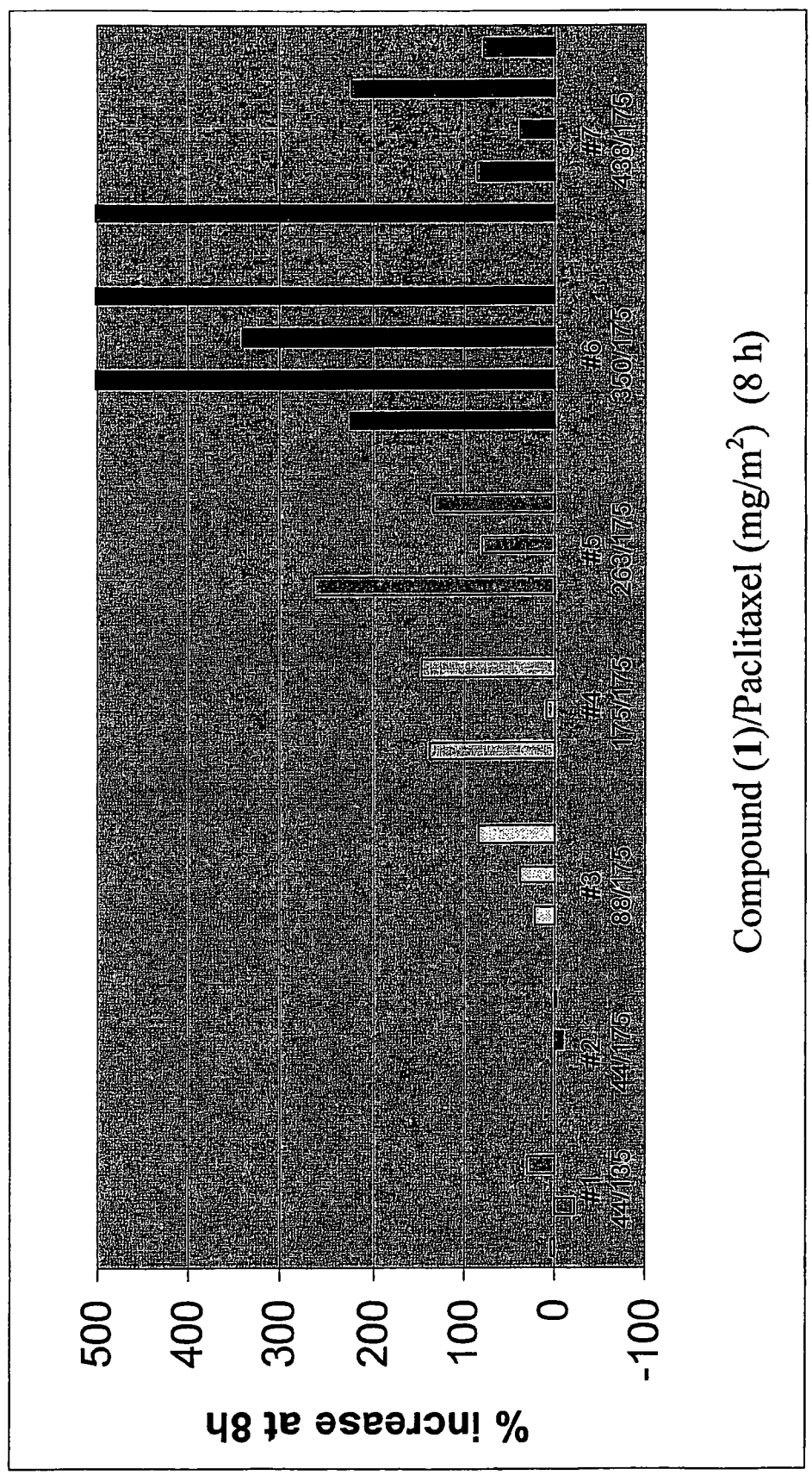

FIGS. 7A, 7B, and 7C are bar graphs showing the percent increase in Hsp70 plasma levels associated with administration of the Compound (1)/paclitaxel combination therapy at 1 hour (FIG. 7A), 5 hours (FIG. 7B), and 8 hours (FIG. 7C) after administration. Significant rises in Hsp70 levels occurred for at least one patient at the 88 mg/m2 (220 µmol/m2) Compound (1) dose, where Hsp70 levels nearly doubled in a percent increase of about 90%. At the 175 mg/m2 (437 µmol/m2) Compound (1) dose, Hsp70 concentrations more than doubled in two patients; at the 263 mg/m2 (657 µmol/m2) Compound (1) dose, Hsp70 concentrations roughly doubled in two patients and increased by more than 250% in a third patient; at the 350 mg/m2 (874 µmol/m2) Compound (1) dose, Hsp70 concentrations increased more than 200% in all patients and increased by as much as 500% in two patients; at the 438 mg/m2 (1094 µmol/m2) Compound (1) dose, Hsp70 concentrations roughly doubled in two patients, increased by over 2005 intone patient, and increased by as much as 500% in another patient.

Thus, the combination of a bi(thio-hydrazide) amide and taxane dramatically increased plasma Hsp70 levels in patients, giving significant increases for patients at a combined paclitaxel dose of 175 mg/m2 (205 µmol/m2) and Compound (1) doses ranging from 88 through 438 mg/m2 (220-1094 µmol/m2). Moreover, the combination was well-tolerated, with adverse events consistent with those expected for paclitaxel alone.

Example 12

A Phase 2 Study on Combination Therapy with Carboplatin Induces Hsp70

The following study of Compound (1) and paclitaxel in patients with non-small cell lung carcinoma was initiated based on the biological activity shown by the results of the above Phase I study, where the combined administration Compound (1) and paclitaxel led to dose-related Hsp70 induction.

Phase 1 (safety/PK/MTD (maximum tolerated dose) was followed by a Phase 2 randomized two arm portion. Two dose levels were evaluated in Phase 1.

Cohort 1 was dosed with carboplatin AUC (area under the curve) 6, paclitaxel 175 mg/m2 and Compound (1) 233 mg/m2. If the maximum tolerated dose was not observed, Cohort 2 was enrolled with carboplatin AUC 6, paclitaxel 200 mg/m2 and Compound (1) 266 mg/m2.

Dosing was IV q 3 weeks for up to 6 cycles in the absence of dose-limiting toxicity or progression. In the phase 2 portion, 86 patients are planned to be randomized 1:1 to carboplatin AUC 6+paclitaxel 200 mg/m2 IV q 3 weeks or carboplatin AUC 6, paclitaxel 200 mg/m2 and Compound (1) 266 mg/m2. The phase 2 primary endpoint is time to progression, with secondary endpoints of response rate, survival, and quality of life. Study pharmacodynamic parameters include NK cell activity and Hsp70 level.

Sixteen patients were treated in Phase 1, 7 in Cohort 1, and 9 in Cohort 2. No first cycle dose-limiting toxicities were seen in either cohort. Phase adverse effects (AEs) included (usually Grade 1-2) arthralgia and myalgia, peripheral neuropathy, rash, nausea, and vomiting, fatigue, alopecia, edema, dehydration, constipation, and decreased blood counts. Eleven patients completed 6 cycles of therapy. Eight patients (50%) achieved a partial response (PR). Seven of the 8 patients with evaluable samples showed increased NK cell activity when assayed 7 days after the second dose.

The carboplatin:paclitaxel:Compound (1) combination is well tolerated at the dose levels studied, and the overall safety profile appears similar to that of carboplatin:paclitaxel alone. Encouraging clinical activity was observed, as well as correlative NK activity that supports a conclusion that Compound (1) is biologically active in vivo.

The RECIST criteria used to determine objective tumor response for target lesions, taking into account the measurement of the longest diameter for all target lesions. RECIST criteria include:

Complete Response (CR): Disappearance of all target lesions

Partial Response (PR): At least a 30% decrease in the sum of the longest diameter (LD) of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started Table 2 shows the substantial anticancer efficacy and NK cell activity results for different subjects. The Effector/Target data shows the ratio of the subjects PBMC cells to the NK assay target cells. The pre and post dose column values show the percent of tumor cells lysed before dosing with Paclitaxel and Compound (1). Best Response indicates an evaluation of the patient's tumor: PR=at least a 30% decrease in the sum of the longest diameters as compared to baseline, while SD indicates less than 20% of an increase and less than 30% of a decrease in the sum of the longest diameters as compared to baseline. Target Lesions indicates the percent change in targeted melanoma lesions in the subjects. NK Activity indicates the change in NK activity before and after dosing.

Table 2 shows that for patients completing the study (#1-#8) there was a substantial decrease in target lesion size for each patient. Also, 5 of the 8 patients completing the study had the best response evaluation category, at least a 30% decrease in the sum of the longest diameters compared to baseline. For NK cell activity, 8 of the 11 original patients showed an increase between pre- and post-dose treatment, though in this example the difference was not significant according to paired t-test (p=0.06).

TABLE 2

| Subject | Effector/Target | % tumor cell lysis | | dosing information | | Best Response | Target Lesions | NK activity |
|---|---|---|---|---|---|---|---|---|
| | | pre-dose | post-dose | Paclitaxel, mg/M$^2$ | Cmpnd (1) mg/M$^2$ | | | |
| 1 | 80:1 | 9.55 | 16.14 | 175 | 233 | SD | −5.9% | increase |
| 2 | 80:1 | 3.12 | 8.76 | 175 | 233 | SD | −30% | increase |
| 3 | 80:1 | 7.84 | 10.05 | 175 | 233 | PR | −67% | increase |
| 4 | 80:1 | 8.4 | 5.5 | 200 | 266 | PR | −38% | decrease |
| 5 | 80:1 | 7.79 | 30.8 | 175 | 233 | PR | −34% | increase |
| 6 | 80:1 | 3.59 | 7.81 | 200 | 266 | PR | −44% | increase |
| 7 | 80:1 | 0.92 | 7.75 | 175 | 233 | SD | −24% | no change |
| 8 | 80:1 | 10.7 | 14.61 | 175 | 233 | PR | −62% | increase |
| 9 | 80:1 | 7.21 | 10.11 | | | NA | NA | increase |
| 10 | 80:1 | 8 | 3.8 | | | NA | NA | decrease |
| 11 | 80:1 | 36.19 | 45.98 | | | NA | NA | increase |

Given the safety profile of Cohort 2, this dose level (carboplatin AUC 6, paclitaxel 200 mg/m2 and Compound (1) 266 mg/m2) was used in Phase 2.

Example 13

A 2 Stage Phase 2 Study on Combination Therapy Induces Hsp70

The following study of Compound (1) and paclitaxel in patients with advanced meatstatic melanoma was initiated based on the biological activity shown by the results of the above Phase I study, where the combined administration Compound (1) and paclitaxel led to dose-related Hsp70 induction.

The study included a Stage 1 initial safety assessment of the weekly dose schedule, where Compound (1) 106 mg/m2 (265 µmol/m2) and paclitaxel at 80 mg/m2 (94 µmol/m2) were administered weekly for 3 weeks out a 4 week period. The dose of Compound (1) was then escalated to 213 mg/m2 (532 µmol/m2) in combination with the paclitaxel at 80 mg/m2 (94 µmol/m2). The higher tolerated dose level was expanded to a total of 20 patients (Stage 1).

A total of 7 patients were treated in the initial safety assessment, 3 at the lower dose level and 4 at the higher. In the absence of dose-limiting toxicities in either group, the higher dose level was chosen as the dose of interest and additional patients were enrolled to complete stage 1. Adverse events seen were as expected for paclitaxel chemotherapy administration. Of 20 evaluable patients, 11 were stable at 3 months for 55% NPR.

The study will continue to Stage 2 if 7 or more patients have a response of stable disease or better, or at least 2 patients have a partial response or better. A safety assessment was performed with the first 6 patients enrolled as the weekly dose schedule had not previously been studied in humans. The primary endpoint is non-progression rate (NPR) at 3 months and response rate. Pharmacodynamic parameters include pre and post-dose NK cell activity in blood and when possible, tumor biopsies.

Table 3 shows the significant preliminary results of anti-cancer efficacy and NK cell activity results when assayed 7 days after the second dose for different subjects. The Effector/Target data shows the ratio of the subjects PBMC cells to the NK assay target cells. The pre and post dose column values show the percent of tumor cells lysed before dosing with Paclitaxel and Compound (1). Best Response indicates an evaluation of the patient's tumor: SD indicates less than 20% of an increase and less than 30% of a decrease in the sum of the longest diameters as compared to baseline; and PD=at least a 20% increase in the sum of the longest diameters as compared to baseline. NK Activity indicates the change in NK activity before and after dosing.

Table 3 shows that for patients completing the study (#12-#20, 422), three patients had less than 20% of an increase and less than 30% of a decrease in the sum of the longest diameters as compared to baseline, while seven patients had at least a 20% increase in the sum of the longest diameters as compared to baseline. For NK cell activity, four of the original patients showed a statistically significant increase between pre- and post-dose treatment.

TABLE 3

| Subject | Effector/Target | % tumor cell lysis | | dosing information | | Best Response | NK activity |
|---|---|---|---|---|---|---|---|
| | | pre-dose | post-dose | Paclitaxel, mg/M$^2$ | Cmpnd (1) mg/M$^2$ | cycle 2 week 4 | |
| 12 | 80:1 | 2.32 | 7.74 | 80 | 106 | SD | increase |
| 13 | 80:1 | 6.13 | 2.43 | 80 | 106 | PD | decrease |
| 14 | 80:1 | 3.83 | 10.77 | 80 | 213 | SD | increase |
| 15 | (40:1) | 3.5 | 10.01 | 80 | 213 | PD | (increase) |
| 16 | 80:1 | 19.71 | 19.78 | 80 | 213 | SD | no change |
| 17 | 80:1 | 41.61 | 26.52 | 80 | 213 | PD | decrease |
| 18 | 80:1 | 8.6 | 8.64 | 80 | 213 | PD | no change |
| 19 | 80:1 | 24.76 | 18.77 | 80 | 213 | PD | decrease |
| 20 | 80:1 | 16.49 | 5.2 | 80 | 213 | PD | decrease |
| 21 | 80:1 | 15.4 | 26.31 | 80 | 213 | NA | increase |
| 22 | 80:1 | 10.81 | 7.2 | 80 | 213 | PD | decrease |

The combination therapy was well-tolerated on the weekly schedule. Enrollment in the randomized portion will assess the activity of Compound (1) in combination with paclitaxel versus paclitaxel alone.

Stage 2 is planned to be a randomized 2-arm study comparing the drug combination to paclitaxel alone. The criterion for continuation to Stage 2 is >=50% non-progression rate (NPR) at two months. A total of 78 patients are to be randomized 2:1 (combination:control). The primary endpoint is time to progression; secondary endpoints are response rate, survival, and quality of life. Pharmacodynamic parameters will include pre- and post-dose measurements of NK cell activity in blood and, when possible, tumor biopsies.

Example 14

A Phase 2 Study on Combination Therapy Induces Hsp70

The following study of Compound (1) and paclitaxel in patients with soft tissue sarcomas was initiated based on the biological activity shown by the results of the above Phase I study, where the combined administration Compound (1) and paclitaxel led to dose-related Hsp70 induction.

The study is a 2 stage design, enrolling 30 patients in the first stage and adding 50 patients to total 80 if certain continuation criteria are met. Major inclusion criteria are refractory or recurrent soft tissue sarcomas other than gastrointestinal stromal tumor (GIST), with evidence of recent progression. Patients are treated weekly, 3 weeks out of every 4 week cycle with 213 mg/m2 Compound (1) and 80 mg/m2 paclitaxel. For example, the compounds were administered together 3 weeks out of 4 on Days 1, 8, and 15 of a 28 day cycle as a 1 hour IV infusion. 30 Patients have been enrolled to completed accrual of Stage 1.

As used herein, "soft-tissue sarcomas" (STS) are cancers that begin in the soft tissues that support, connect, and surround various parts of the body for example, soft tissues such as muscles, fat, tendons, nerves, and blood vessels, lymph nodes, or the like. Such STSs can occur anywhere in the body, though typically about one half occur in the limbs. In various embodiments, STSs can include one or more cancers selected from liposarcoma, fibrosarcoma, malignant fibrous histiocytoma leiomyosarcoma, neurofibrosarcoma, rhabdomyosarcoma, synovial sarcoma, or the like.

Table 4 shows the significant preliminary results of anticancer efficacy and NK cell activity results when assayed 7 days after the second dose for different subjects. The Effector/Target data shows the ratio of the subjects PBMC cells to the NK assay target cells. The pre and post dose column values show the percent of tumor cells lysed before dosing with Paclitaxel and Compound (1). Best Response indicates an evaluation of the patient's tumor: PR=at least a 30% decrease in the sum of the longest diameters as compared to baseline; SD indicates less than 20% of an increase and less than 30% of a decrease in the sum of the longest diameters as compared to baseline; and PD=at least a 20% increase in the sum of the longest diameters as compared to baseline. NK Activity indicates the change in NK activity before and after dosing.

Table 4 shows that for patients completing the study (#23-#29, #31-33), five patients had less than 20% of an increase and less than 30% of a decrease in the sum of the longest diameters as compared to baseline, while five patients had at least a 20% increase in the sum of the longest diameters as compared to baseline. For NK cell activity, seven of the original patients showed a statistically significant increase or no change between pre- and post-dose treatment, while only four of the original patients showed a decrease statistically significant increase between pre- and post-dose treatment.

TABLE 4

| Subject | Effector/ Target | % tumor cell lysis | | dosing information | | Best Response | |
|---|---|---|---|---|---|---|---|
| | | pre-dose | post-dose | Paclitaxel, mg/M$^2$ | Cmpnd (1) mg/M$^2$ | cycle 2 | NK activity |
| 23 | 80:1 | 4.28 | 30.48 | 80 | 213 | PD | increase |
| 24 | 80:1 | 20.74 | 20.04 | 80 | 213 | SD | no change |
| 25 | 80:1 | 34.28 | 11.86 | 80 | 213 | PD | decrease |
| 26 | 80:1 | 22.33 | 14.74 | 80 | 213 | SD | decrease |
| 27 | 80:1 | 10.6 | 22.9 | 80 | 213 | SD | increase |
| 28 | 80:1 | 17.93 | 28.13 | 80 | 213 | SD | increase |
| 29 | 80:1 | 6.58 | 17.18 | 80 | 213 | PD | increase |
| 30 | (40:1) | 9.88 | 9.91 | 80 | 213 | NA | no change |
| 31 | 80:1 | 2.62 | 5.46 | 80 | 213 | SD | increase |
| 32 | 80:1 | 13.03 | 7.41 | 80 | 213 | PD | decrease |
| 33 | 80:1 | 15.77 | 7.84 | 80 | 213 | PD | decrease |

Patients are currently being evaluated through 3 months. Adverse events seen were typical for paclitaxel administration on a similar schedule. Assessment of NK activity is ongoing. The addition of Compound (1) to the weekly paclitaxel schedule was well-tolerated. Stage 1 accrual has completed, and patients are currently being evaluated for the study continuation decision.

The entire teachings of each cited document is incorporated herein by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method to ameliorate a Hsp70-responsive disorder in a subject, comprising administering to the subject an effective amount of a compound represented by the following Structural Formula:

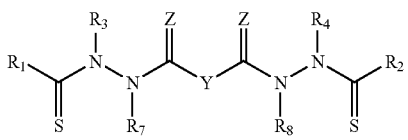

or a pharmaceutically acceptable salt thereof, wherein:
Y is a covalent bond or an optionally substituted straight chained hydrocarbyl group, or, Y, taken together with both >C=Z groups to which it is bonded, is an optionally substituted aromatic group;

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;

$R_7$-$R_8$ are independently —H, an optionally substituted aliphatic group, or an optionally substituted aryl group; and Z is O or S;

wherein the HSP-70 responsive disorder is inflammation due to infection.

2. The method of claim 1, wherein the compound is administered as a monotherapy.

3. The method of claim 1, wherein the compound is a disodium or dipotassium salt.

4. The method of claim 1 wherein Z is O, $R_1$ and $R_2$ are the same and $R_3$ and $R_4$ are the same.

5. The method of claim 4, wherein:
Y is a covalent bond, —C($R_5R_6$)—, —(CH$_2$CH$_2$)—, trans-(CH=CH)—, cis-(CH=CH)— or —(C≡C)—; and
$R_5$ and $R_6$ are each independently —H, an aliphatic or substituted aliphatic group, or $R_5$ is —H and $R_6$ is an optionally substituted aryl group, or, $R_5$ and $R_6$, taken together, are an optionally substituted C2-C6 alkylene group.

6. The method of claim 5, wherein:
Y is —C($R_5R_6$)—;
$R_1$ and $R_2$ are each an optionally substituted aryl group; and
$R_3$ and $R_4$ are each an optionally substituted aliphatic group.

7. The method of claim 6, wherein $R_5$ is —H and $R_6$ is —H, an aliphatic or substituted aliphatic group.

8. The method of claim 7, wherein $R_3$ and $R_4$ are each an alkyl group and $R_6$ is —H or methyl.

9. The method of claim 8, wherein $R_1$ and $R_2$ are each an optionally substituted phenyl group and $R_3$ and $R_4$ are each methyl or ethyl.

10. The method of claim 9, wherein the phenyl group represented by $R_1$ and the phenyl group represented by $R_2$ are optionally substituted with one or more groups selected from: —$R^a$, —OH, —Br, —Cl, —I, —F, —O$R^a$, —O—CO$R^a$, —CO$R^a$, —CN, —NCS, —NO$_2$, —COOH, —SO$_3$H, —NH$_2$, —NH$R^a$, —N($R^aR^b$), —COO$R^a$, —CHO, —CONH$_2$, —CONH$R^a$, —CON($R^aR^b$), —NHCO$R^a$, —N$R^c$CO$R^a$, —NHCONH$_2$, —NHCON$R^a$H, —NHCON($R^aR^b$), —N$R^c$CONH$_2$, —N$R^c$CON$R^a$H, —N$R^c$CON($R^aR^b$), —C(=NH)—NH$_2$, —C(=NH)—NH$R^a$, —C(=NH)—N($R^aR^b$), —C(=N$R^c$)—NH$_2$, —C(=N$R^c$)—NH$R^a$, —C(=N$R^c$)—N($R^aR^b$), —NH—C(=NH)—NH$_2$, —NH—C(=NH)—NH$R^a$, —NH—C(=NH)—N($R^aR^b$), —NH—C(=N$R^c$)—NH$_2$, —NH—C(=N$R^c$)—NH$R^a$, —NH—C(=N$R^c$)—N($R^aR^b$), —N$R^d$—C(=NH)—NH$_2$, —N$R^d$—C(=NH)—NH$R^a$, —N$R^d$—C(=NH)—N($R^aR^b$), —N$R^d$—C(=N$R^c$)—NH$_2$, —N$R^d$—C(=N$R^c$)—NH$R^a$, —N$R^d$—C(=N$R^c$)—N($R^aR^b$), —NHNH$_2$, —NHNH$R^a$, —NHN$R^aR^b$, —SO$_2$NH$_2$, —SO$_2$NH$R^a$, —SO$_2$N$R^aR^b$, —CH=CH$R^a$, —CH=C$R^aR^b$, —C$R^c$=C$R^aR^b$, —C$R^c$=CH$R^a$, —C$R^c$=C$R^aR^b$, —CC$R^a$, —SH, —S$R^a$, —S(O)$R^a$, —S(O)$_2$$R^a$, wherein $R^a$-$R^d$ are each independently an alkyl group, aromatic group, non-aromatic heterocyclic group; or, —N($R^aR^b$), taken together, form an optionally substituted non-aromatic heterocyclic group, wherein the alkyl, aromatic and non-aromatic heterocyclic group represented by $R^a$-$R^d$ and the non-aromatic heterocyclic group represented by —N($R^aR^b$) are each optionally and independently substituted with one or more groups represented by $R^\#$, wherein $R^\#$ is $R^+$, —O$R^+$, —O(haloalkyl), —S$R^+$, —NO$_2$, —CN, —NCS, —N($R^+$)$_2$, —NHCO$_2R^+$, —NHC(O)$R^+$, —NHNHC(O)$R^+$, —NHC(O)N($R^+$)$_2$, —NHNHC(O)N($R^+$)$_2$, —NHNHCO$_2R^+$, —C(O)C(O)$R^+$, —C(O)CH$_2$C(O)$R^+$, —CO$_2R^+$, —C(O)$R^+$, C(O)N($R^+$)$_2$, —OC(O)$R^+$, —OC(O)N($R^+$)$_2$, —S(O)$_2R^+$, —SO$_2$N($R^+$)$_2$, —S(O)$R^+$, —NHSO$_2$N($R^+$)$_2$, —NHSO$_2R^+$, —C(=S)N($R^+$)$_2$, or —C(=NH)—N($R^+$)$_2$; wherein $R^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine; or —N($R^+$)$_2$ is a non-aromatic heterocyclic group, provided that non-aromatic heterocyclic groups represented by $R^+$ and —N($R^+$)$_2$ that comprise a secondary ring amine are optionally acylated or alkylated.

11. The method of claim 10, wherein the phenyl groups represented by $R_1$ and $R_2$ are optionally substituted with C1-C4 alkyl, C1-C4 alkoxy, C1-C4 haloalkyl, C1-C4 haloalkoxy, phenyl, benzyl, pyridyl, —OH, —NH$_2$, —F, —Cl, —Br, —I, —NO$_2$ or —CN.

12. The method of claim 5, wherein:
Y is —C$R_5R_6$—;
$R_1$ and $R_2$ are both an optionally substituted aliphatic group;
$R_5$ is —H; and
$R_6$ is —H or an optionally substituted aliphatic group.

13. The method of claim 12, wherein $R_1$ and $R_2$ are both a C3-C8 cycloalkyl group optionally substituted with at least one alkyl group.

14. The method of claim 13, wherein $R_3$ and $R_4$ are both an alkyl group; and $R_6$ is —H or methyl.

15. The method of claim 14, wherein $R_1$ and $R_2$ are both cyclopropyl or 1-methylcyclopropyl.

16. A method to ameliorate a Hsp70-responsive disorder in a subject, comprising administering to the subject an effective amount of a compound represented by the following Structural Formula:

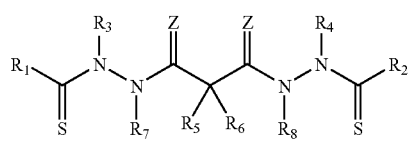

or a pharmaceutically acceptable salt thereof, wherein:
$R_7$-$R_8$ are both —H, and:
$R_1$ and $R_2$ are both phenyl, $R_3$ and $R_4$ are both methyl, and $R_5$ and $R_6$ are both —H;

$R_1$ and $R_2$ are both phenyl, $R_3$ and $R_4$ are both ethyl, and $R_5$ and $R_6$ are both —H;

$R_1$ and $R_2$ are both 4-cyanophenyl, $R_3$ and $R_4$ are both methyl, $R_5$ is methyl, and $R_6$ is —H;

$R_1$ and $R_2$ are both 4-methoxyphenyl, $R_3$ and $R_4$ are both methyl, and $R_5$ and $R_6$ are both —H;

$R_1$ and $R_2$ are both phenyl, $R_3$ and $R_4$ are both methyl, $R_5$ is methyl, and $R_6$ is —H;

$R_1$ and $R_2$ are both phenyl, $R_3$ and $R_4$ are both ethyl, $R_5$ is methyl, and $R_6$ is —H;

$R_1$ and $R_2$ are both 4-cyanophenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, $R_5$ is methyl, and $R_6$ is —H;

$R_1$ and $R_2$ are both 3-cyanophenyl, $R_3$ and $R_4$ are both methyl, and $R_5$ and $R_6$ are both —H;

$R_1$ and $R_2$ are both 3-fluorophenyl, $R_3$ and $R_4$ are both methyl, and $R_5$ and $R_6$ are both —H;

$R_1$ and $R_2$ are both 4-chlorophenyl, $R_3$ and $R_4$ are both methyl, $R_5$ is methyl, and $R_6$ is —H;

$R_1$ and $R_2$ are both 2-methoxyphenyl, $R_3$ and $R_4$ are both methyl, and $R_5$ and $R_6$ are both —H;

$R_1$ and $R_2$ are both 3-methoxyphenyl, $R_3$ and $R_4$ are both methyl, and $R_5$ and $R_6$ are both —H;

$R_1$ and $R_2$ are both 2,3-dimethoxyphenyl, $R_3$ and $R_4$ are both methyl, and $R_5$ and $R_6$ are both —H;

$R_1$ and $R_2$ are both 2,3-dimethoxyphenyl, $R_3$ and $R_4$ are both methyl, $R_5$ is methyl, and $R_6$ is —H;

$R_1$ and $R_2$ are both 2,5-difluorophenyl, $R_3$ and $R_4$ are both methyl, and $R_5$ and $R_6$ are both —H;

$R_1$ and $R_2$ are both 2,5-difluorophenyl, $R_3$ and $R_4$ are both methyl, $R_5$ is methyl, and $R_6$ is —H;

$R_1$ and $R_2$ are both 2,5-dichlorophenyl, $R_3$ and $R_4$ are both methyl, and $R_5$ and $R_6$ are both —H;

$R_1$ and $R_2$ are both 2,5-dimethylphenyl, $R_3$ and $R_4$ are both methyl, and $R_5$ and $R_6$ are both —H;

wherein the HSP-70 responsive disorder is inflammation due to infection.

17. The method of claim 16, wherein the compound is represented by the following Structural Formula:

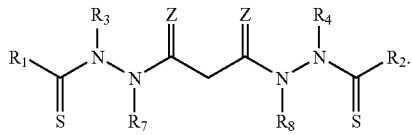

IIIb

18. The method of claim 16, wherein the compound is represented by the following Structural Formula:

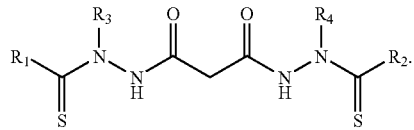

IVb

19. The method of claim 16, wherein the compound is a disodium salt.

20. A method to ameliorate a Hsp70-responsive disorder in a subject, comprising administering to the subject an effective amount of a compound represented by one of the following Structural Formulas:

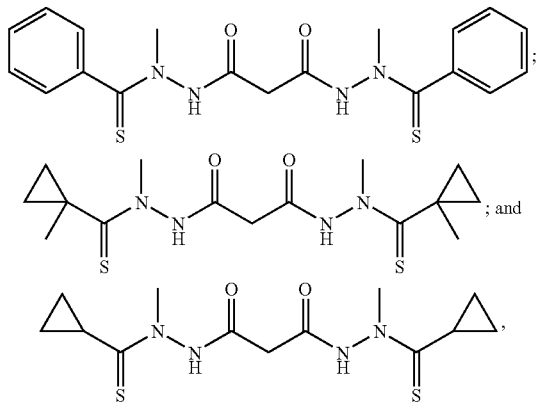

or a pharmaceutically acceptable salt thereof,
wherein the HSP-70 responsive disorder is inflammation due to infection.

21. The method of claim 20, wherein the compound is represented by the following Structural Formula:

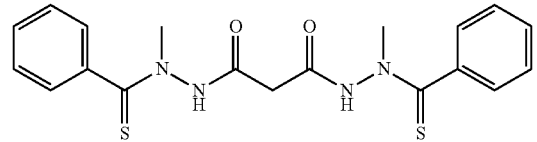

or a pharmaceutically acceptable salt thereof.

22. The method of claim 20, wherein the compound is a disodium salt.

* * * * *

UNITED STATES PATENT AND TRADEMARK OFFICE
CERTIFICATE OF CORRECTION

| | | |
|---|---|---|
| PATENT NO. | : 8,148,426 B2 | Page 1 of 1 |
| APPLICATION NO. | : 11/281923 | |
| DATED | : April 3, 2012 | |
| INVENTOR(S) | : Barsoum et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 607 days.

Signed and Sealed this
Fourteenth Day of August, 2012

David J. Kappos
*Director of the United States Patent and Trademark Office*